US009826733B2

(12) United States Patent
Vom et al.

(10) Patent No.: US 9,826,733 B2
(45) Date of Patent: Nov. 28, 2017

(54) METHOD, SYSTEM AND APPARATUS FOR IMPROVED MICROMANIPULATION AND STORAGE

(71) Applicant: GENEA LIMITED, Sydney (AU)

(72) Inventors: Eduardo Vom, Box Hill (AU); Tammie Kim Roy, Alexandria (AU); Craig Matthews Lewis, Box Hill (AU); Benjamin Rawlingson Hobbs, Box Hill (AU); Simon James Hobbs, Box Hill (AU)

(73) Assignee: Genea IP Holdings Pty Limited, Sydney (AU)

( * ) Notice: Subject to any disclaimer, the term of this patent is extended or adjusted under 35 U.S.C. 154(b) by 88 days.

(21) Appl. No.: 14/759,419

(22) PCT Filed: Jan. 7, 2014

(86) PCT No.: PCT/AU2014/000005
§ 371 (c)(1),
(2) Date: Jul. 7, 2015

(87) PCT Pub. No.: WO2014/106286
PCT Pub. Date: Jul. 10, 2014

(65) Prior Publication Data
US 2015/0351381 A1    Dec. 10, 2015

(30) Foreign Application Priority Data
Jan. 7, 2013    (AU) .............................. 2013900039

(51) Int. Cl.
*A01N 1/02*    (2006.01)
*G05B 15/00*    (2006.01)
(Continued)

(52) U.S. Cl.
CPC ......... *A01N 1/0252* (2013.01); *A01N 1/0242* (2013.01); *A01N 1/0257* (2013.01);
(Continued)

(58) Field of Classification Search
CPC .. A01N 1/0252; A01N 1/0242; A01N 1/0268; G05B 15/02; G05D 7/0617
(Continued)

(56) References Cited

U.S. PATENT DOCUMENTS 6,000,603 A    12/1999  Koskenmaki et al.
6,408,878 B2   6/2002   Unger et al.
(Continued)

FOREIGN PATENT DOCUMENTS

WO    2009/105813 A1    9/2009
WO    2011/146998 A1    12/2011
WO    2011/160430 A1    12/2011

OTHER PUBLICATIONS

Zhang, X. et al., Title: "Emerging Technologies in Medical Applications of Minimum Volume Vitrification", Nanomedicine, 2011, vol. 6(6), pp. 1115-1129.

*Primary Examiner* — Fred Prince
(74) *Attorney, Agent, or Firm* — Eversheds Sutherland (US) LLP

(57) ABSTRACT

The present application relates to the manipulation and handling of biological materials and, in one form, provides an apparatus for micromanipulation of biological material, including a channel for accommodating biological material and allowing for passage of liquid treatment solutions. The apparatus may include a two part construction wherein two portions of the apparatus are adapted to be heat sealed with a secondary material intermediate the two portions prior to a vitrification process step. A system for vitrification of a biological specimen is also provided including a software (Continued)

Illustration of the principle module operable means for controlling the temperature environment, a software operable means for controlling fluid dispense volume and velocity and aspiration volume and velocity for the application of liquid treatment solutions to the biological specimen, and a software operable means for controlling protocol time.

14 Claims, 13 Drawing Sheets

(51) Int. Cl.
  *G05D 7/00* (2006.01)
  *G05B 15/02* (2006.01)
  *G05D 7/06* (2006.01)

(52) U.S. Cl.
  CPC .......... *A01N 1/0268* (2013.01); *G05B 15/02* (2013.01); *G05D 7/0617* (2013.01)

(58) Field of Classification Search
  USPC ....... 210/605, 767, 780, 800, 143, 138, 139, 210/175; 435/325, 1.3, 2; 700/258
  See application file for complete search history.

(56) References Cited

U.S. PATENT DOCUMENTS

| | | |
|---|---|---|
| 6,793,753 B2 | 9/2004 | Unger et al. |
| 6,818,395 B1 | 11/2004 | Quake et al. |
| 6,899,137 B2 | 5/2005 | Unger et al. |
| 6,911,345 B2 | 6/2005 | Quake et al. |
| 6,929,030 B2 | 8/2005 | Unger et al. |
| 7,040,338 B2 | 5/2006 | Unger et al. |
| 7,052,545 B2 | 5/2006 | Quake et al. |
| 7,144,616 B1 | 12/2006 | Unger et al. |
| 7,169,314 B2 | 1/2007 | Unger et al. |
| 7,195,670 B2 | 3/2007 | Hansen et al. |
| 7,216,671 B2 | 5/2007 | Unger et al. |
| 7,217,321 B2 | 5/2007 | Hansen et al. |
| 7,244,402 B2 | 7/2007 | Hansen et al. |
| 7,250,128 B2 | 7/2007 | Unger et al. |
| 7,306,672 B2 | 12/2007 | Hansen et al. |
| 7,326,296 B2 | 2/2008 | Quake et al. |
| 7,459,022 B2 | 12/2008 | Hansen et al. |
| 7,462,449 B2 | 12/2008 | Quake |
| 7,479,186 B2 | 1/2009 | Quake et al. |
| 7,494,555 B2 | 2/2009 | Unger et al. |
| 7,501,245 B2 | 3/2009 | Quake et al. |
| 7,601,270 B1 | 10/2009 | Unger et al. |
| 7,670,429 B2 | 3/2010 | Quake et al. |
| 7,704,322 B2 | 4/2010 | Hansen et al. |
| 7,754,010 B2 | 7/2010 | Unger et al. |
| 7,766,055 B2 | 8/2010 | Unger et al. |
| 7,927,422 B2 | 4/2011 | Hansen et al. |
| 8,002,933 B2 | 8/2011 | Unger et al. |
| 8,021,480 B2 | 9/2011 | Hansen et al. |
| 8,052,792 B2 | 11/2011 | Hansen et al. |
| 8,104,497 B2 | 1/2012 | Unger et al. |
| 8,104,515 B2 | 1/2012 | Unger et al. |
| 8,124,218 B2 | 2/2012 | Unger et al. |
| 8,220,487 B2 | 7/2012 | Unger et al. |
| 8,382,896 B2 | 2/2013 | Hansen et al. |
| 8,550,119 B2 | 10/2013 | Unger et al. |
| 8,656,985 B2 | 2/2014 | Rodriquez |
| 2001/0020636 A1 | 9/2001 | Koskenmaki et al. |
| 2001/0029983 A1 | 10/2001 | Unger et al. |
| 2001/0033796 A1 | 10/2001 | Unger et al. |
| 2001/0054778 A1 | 12/2001 | Unger et al. |
| 2002/0025529 A1 | 2/2002 | Quake et al. |
| 2002/0029814 A1 | 3/2002 | Unger et al. |
| 2002/0144738 A1 | 10/2002 | Unger et al. |
| 2002/0145231 A1 | 10/2002 | Quake et al. |
| 2003/0019833 A1 | 1/2003 | Unger et al. |
| 2003/0061687 A1 | 4/2003 | Hansen et al. |
| 2003/0096310 A1 | 5/2003 | Hansen et al. |
| 2004/0115731 A1 | 6/2004 | Hansen et al. |
| 2005/0014175 A1 | 1/2005 | Quake |
| 2005/0062196 A1 | 3/2005 | Hansen et al. |
| 2005/0112882 A1 | 5/2005 | Unger et al. |
| 2005/0147992 A1 | 7/2005 | Quake et al. |
| 2005/0166980 A1 | 8/2005 | Unger et al. |
| 2005/0178317 A1 | 8/2005 | Quake et al. |
| 2005/0205005 A1 | 9/2005 | Hansen et al. |
| 2005/0226742 A1 | 10/2005 | Unger et al. |
| 2005/0229839 A1 | 10/2005 | Quake et al. |
| 2006/0019263 A1 | 1/2006 | Quake et al. |
| 2006/0054228 A1 | 3/2006 | Unger et al. |
| 2006/0172408 A1 | 8/2006 | Quake et al. |
| 2006/0196409 A1 | 9/2006 | Quake et al. |
| 2007/0059494 A1 | 3/2007 | Unger et al. |
| 2007/0169686 A1 | 7/2007 | Quake et al. |
| 2007/0209572 A1 | 9/2007 | Hansen et al. |
| 2007/0209574 A1 | 9/2007 | Hansen et al. |
| 2007/0024903 A1 | 10/2007 | Kitahara et al. |
| 2007/0249038 A1 | 10/2007 | Adamo et al. |
| 2008/0096216 A1 | 4/2008 | Quake |
| 2008/0173365 A1 | 7/2008 | Unger et al. |
| 2008/0182273 A1 | 7/2008 | Hansen et al. |
| 2008/0210319 A1 | 9/2008 | Unger et al. |
| 2008/0210320 A1 | 9/2008 | Unger et al. |
| 2008/0210321 A1 | 9/2008 | Unger et al. |
| 2008/0210322 A1 | 9/2008 | Unger et al. |
| 2008/0220216 A1 | 9/2008 | Unger et al. |
| 2008/0236669 A1 | 10/2008 | Unger et al. |
| 2008/0277005 A1 | 11/2008 | Unger et al. |
| 2008/0277007 A1 | 11/2008 | Unger et al. |
| 2008/0289710 A1 | 11/2008 | Unger et al. |
| 2009/0151422 A1 | 6/2009 | Unger et al. |
| 2009/0168066 A1 | 7/2009 | Hansen et al. |
| 2009/0253141 A1 | 10/2009 | Quake |
| 2010/0175767 A1 | 7/2010 | Unger et al. |
| 2010/0187105 A1 | 7/2010 | Unger et al. |
| 2010/0191382 A1* | 7/2010 | Samuhel ................ B01L 3/545 700/283 |
| 2010/0200782 A1 | 8/2010 | Unger et al. |
| 2010/0263732 A1 | 10/2010 | Hansen et al. |
| 2010/0317108 A1 | 12/2010 | Stojanov |
| 2011/0207112 A1 | 8/2011 | Burbank et al. |
| 2011/0306522 A1 | 12/2011 | Hansen et al. |
| 2012/0046639 A1 | 2/2012 | Hansen et al. |
| 2012/0091374 A1 | 4/2012 | Unger et al. |
| 2012/0241015 A1 | 9/2012 | Hansen et al. |
| 2012/0277912 A1* | 11/2012 | Kirihara ................ B25J 9/1653 700/258 |
| 2012/0328834 A1 | 12/2012 | Unger et al. |
| 2013/0137080 A1 | 5/2013 | Henderson et al. |
| 2013/0204076 A1 | 8/2013 | Han et al. |
| 2014/0041727 A1 | 2/2014 | Hansen et al. |

* cited by examiner

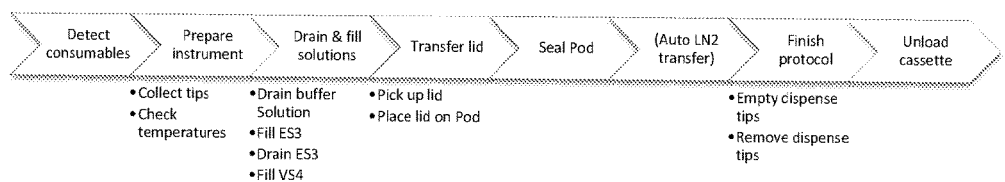
Figure 1 Automated vitrification instrument workflow
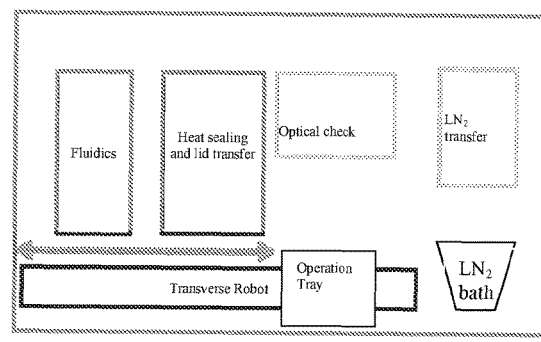
Figure 2 Diagram of instrument layout

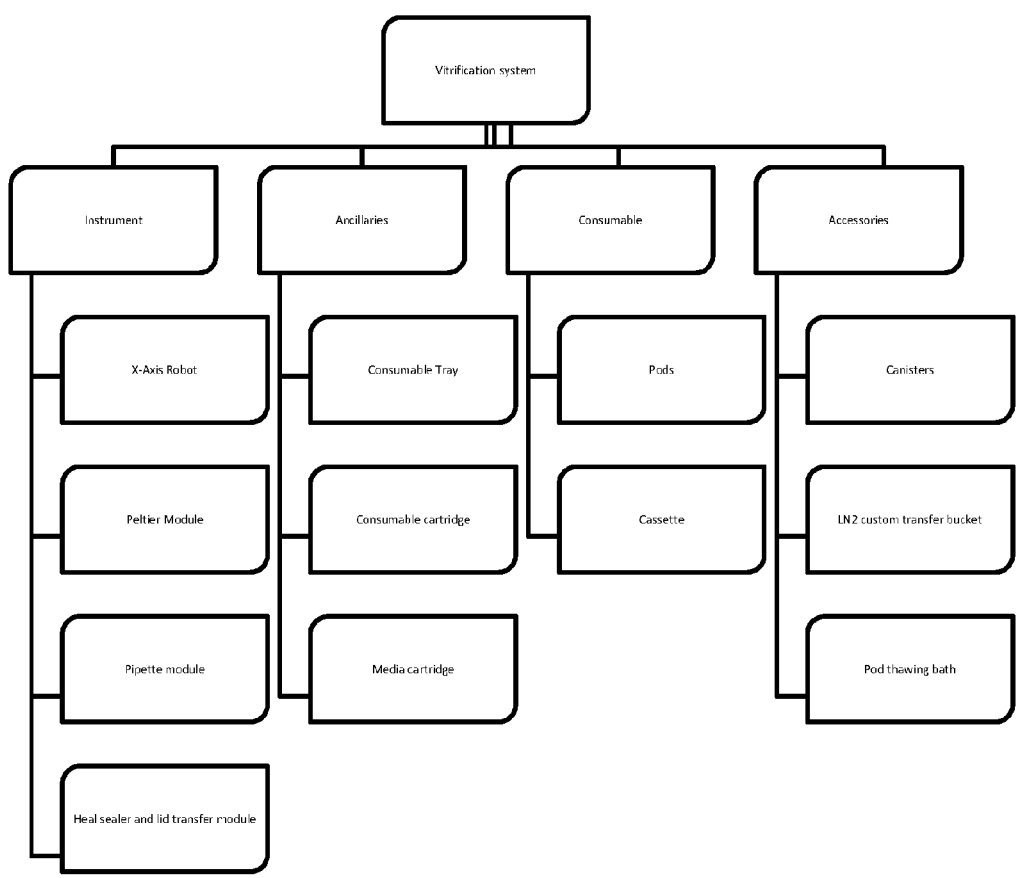
Figure 3 Instrument chart of breakdown of each components

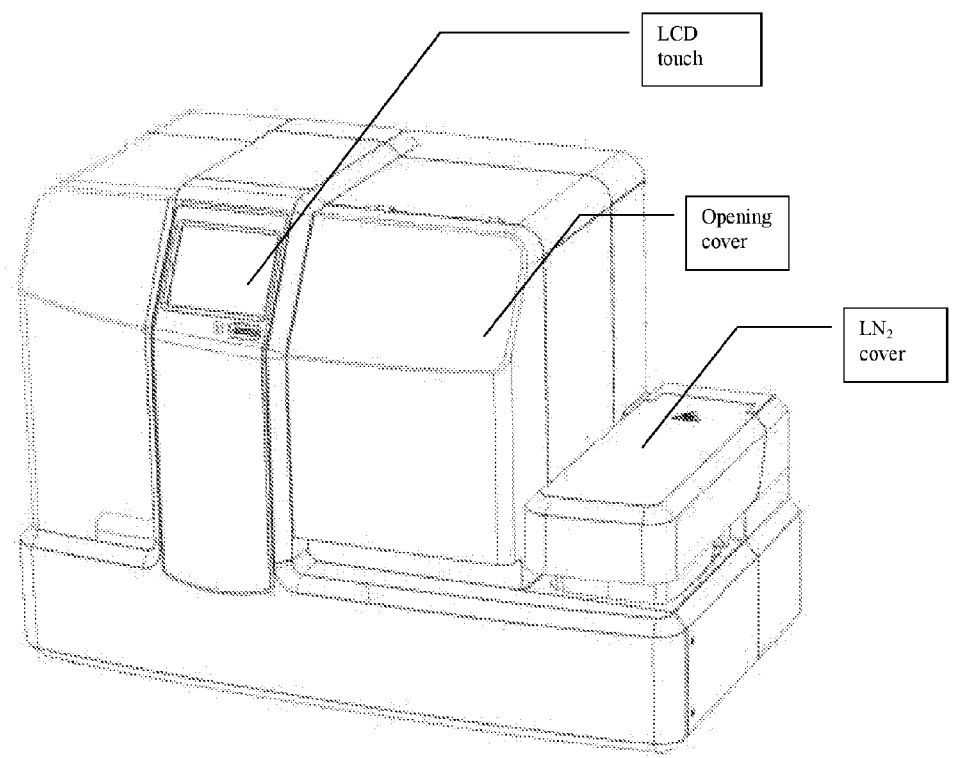
Figure 4 Illustration of instrument with covers

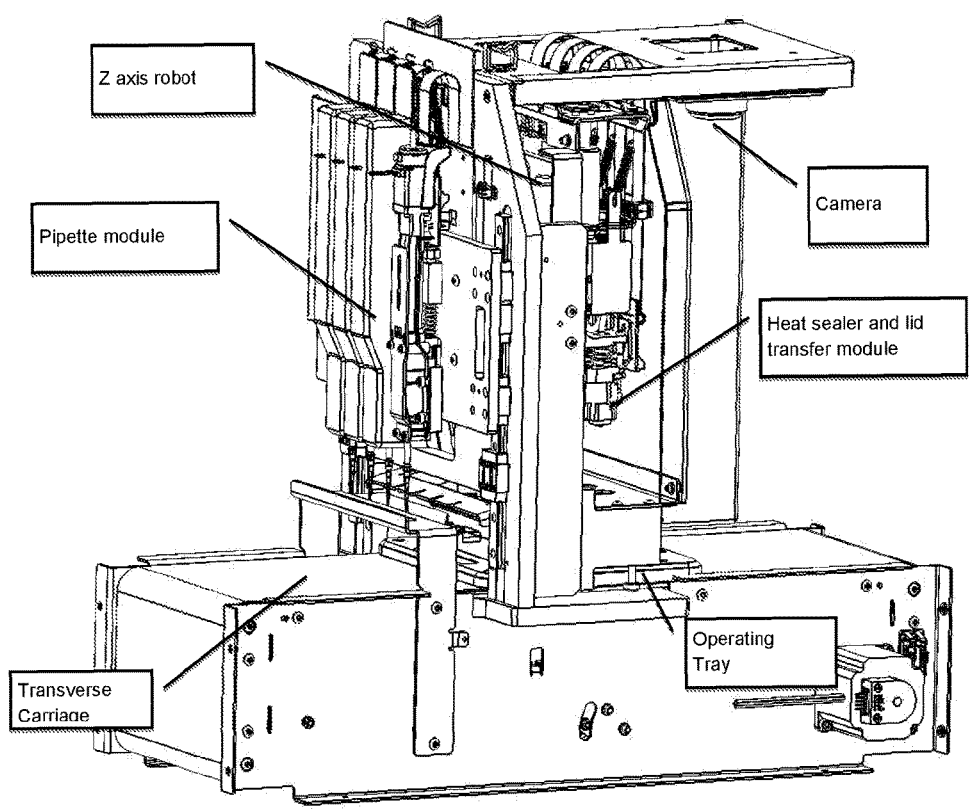
Figure 5 Illustration of the principle module

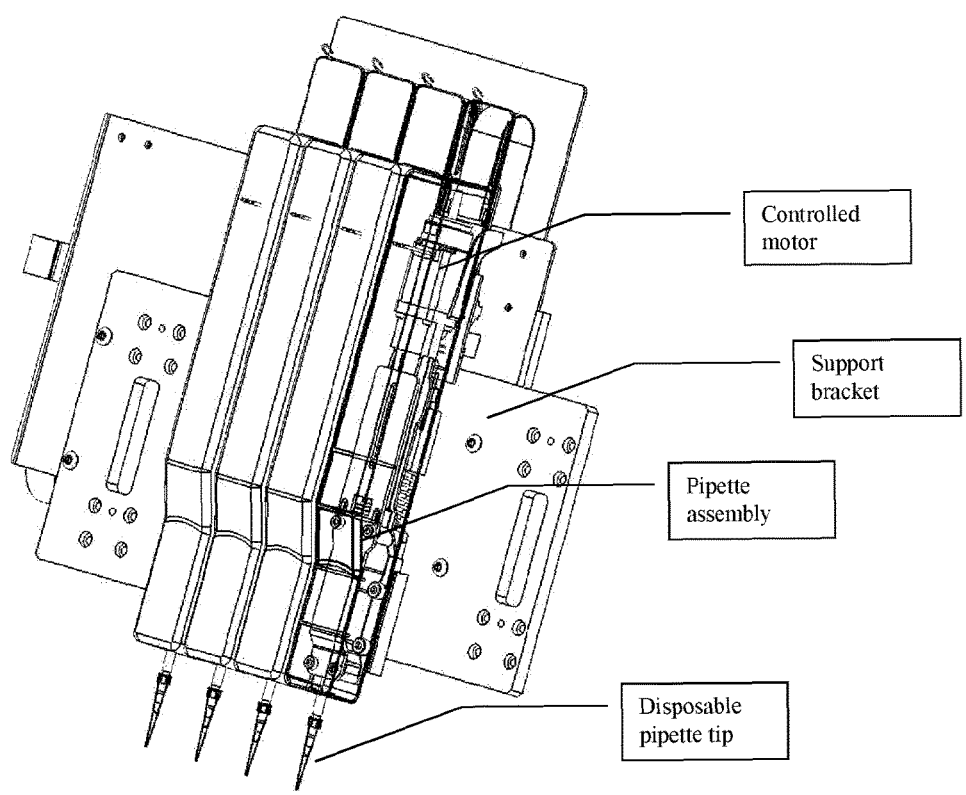
Figure 6 Illustration of the pipette module

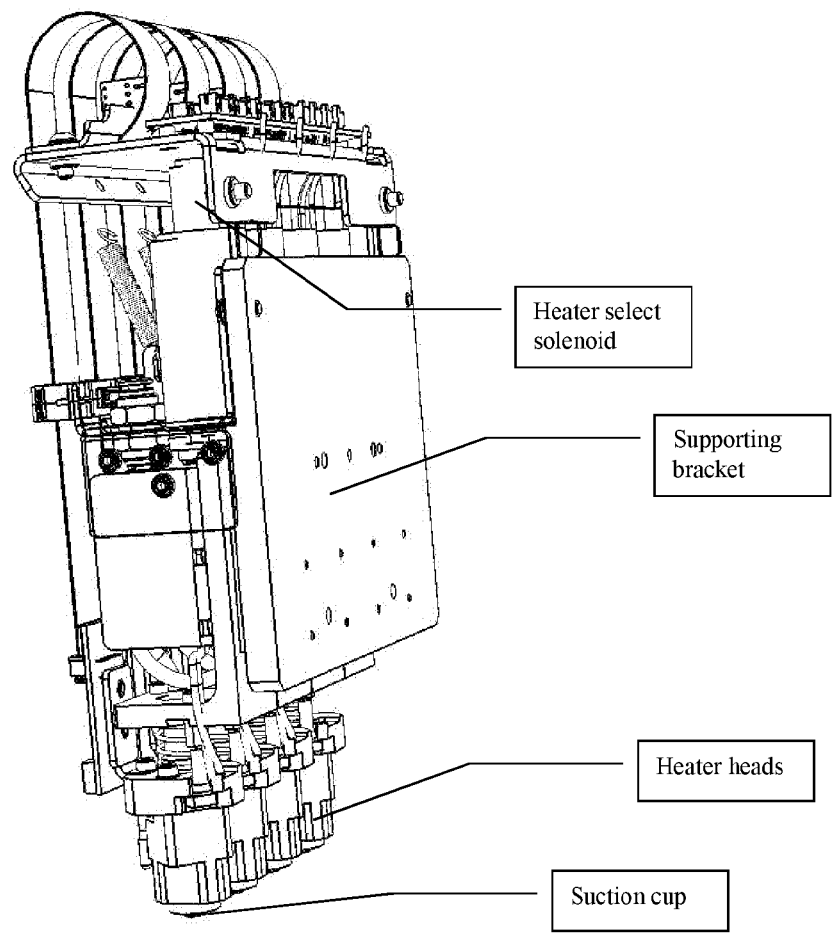
Figure 7 Illustration of the heat sealer and lid transfer module

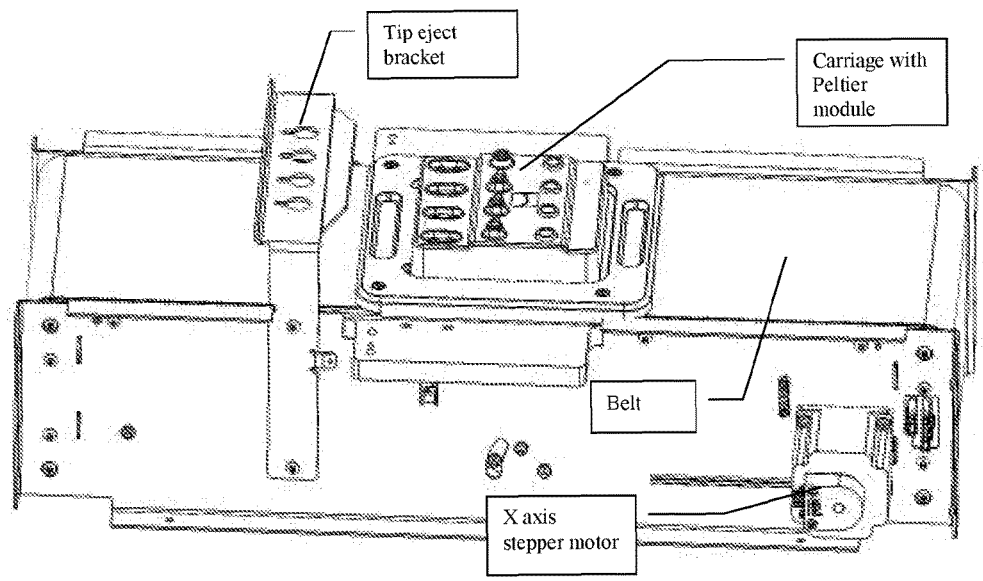
Figure 8 Illustration of the transverse axis assembly
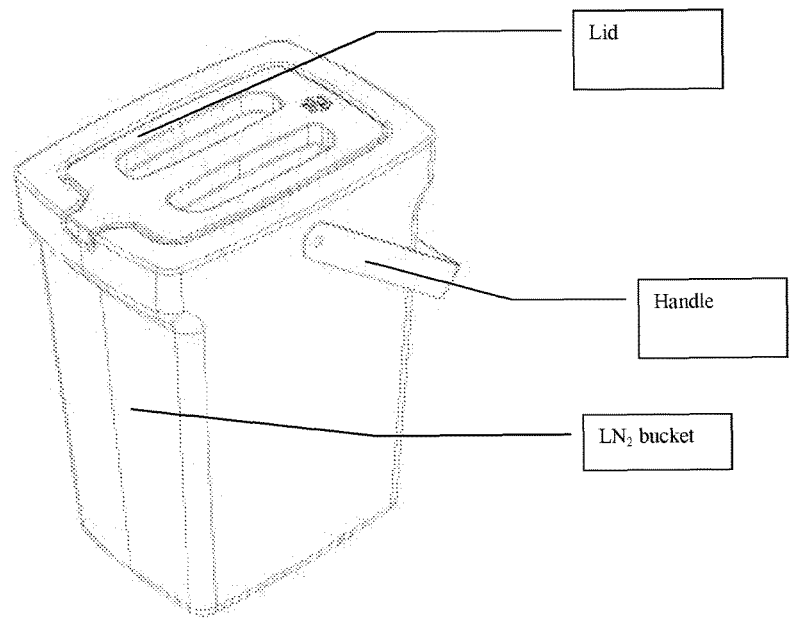
Figure 9 Illustration of the LN₂ transfer bucket

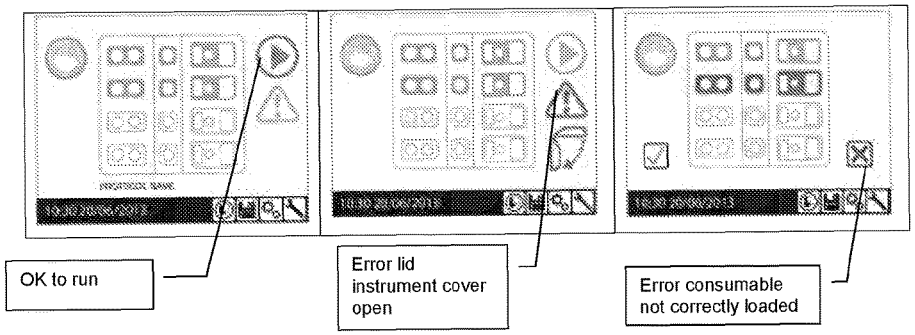
Figure 10 Illustration of the examples of the user interface display
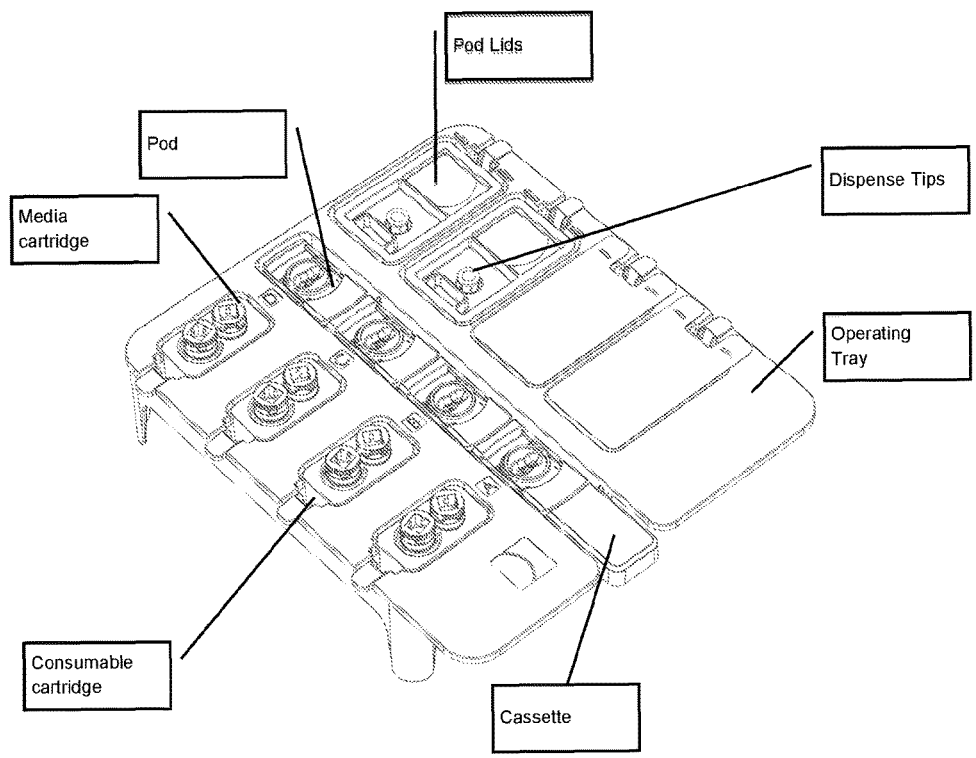
Figure 11 Illustration of the operation tray with all the consumables and media loaded

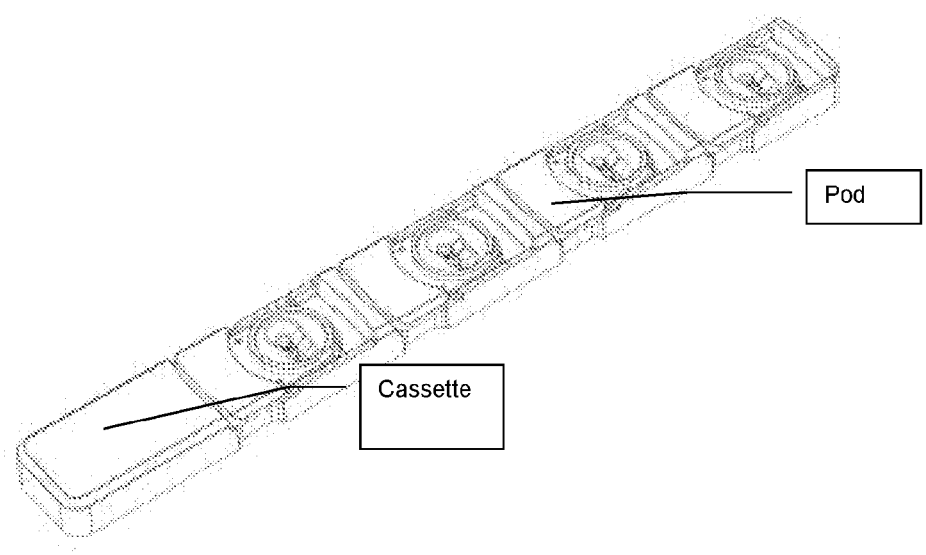
Figure 12 Illustration of the cassette with 4 pods loaded
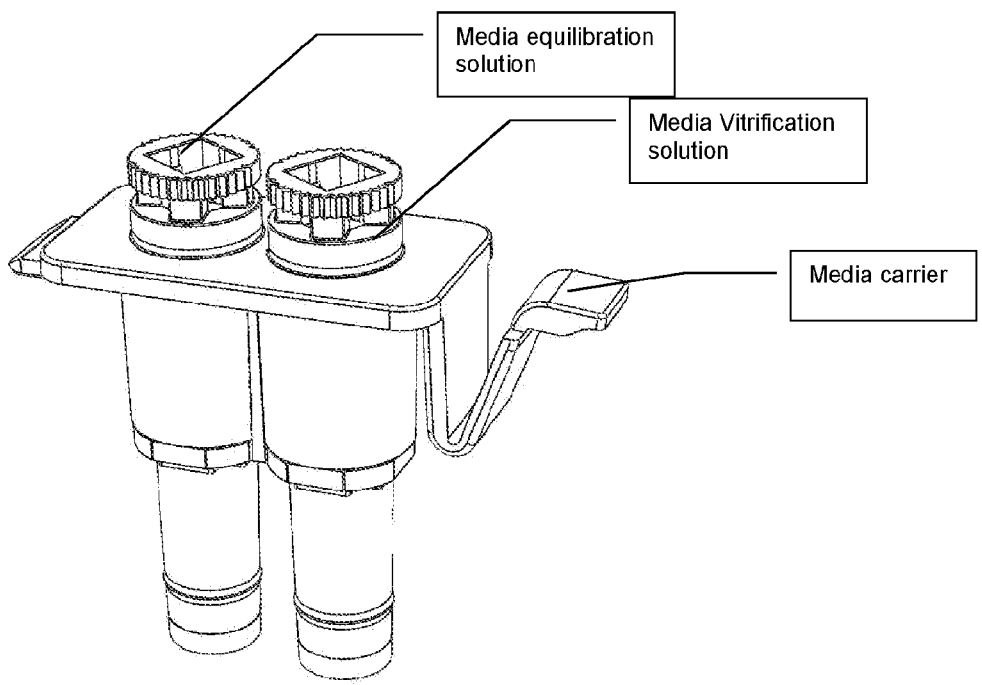
Figure 13 Illustration of the media cartridge

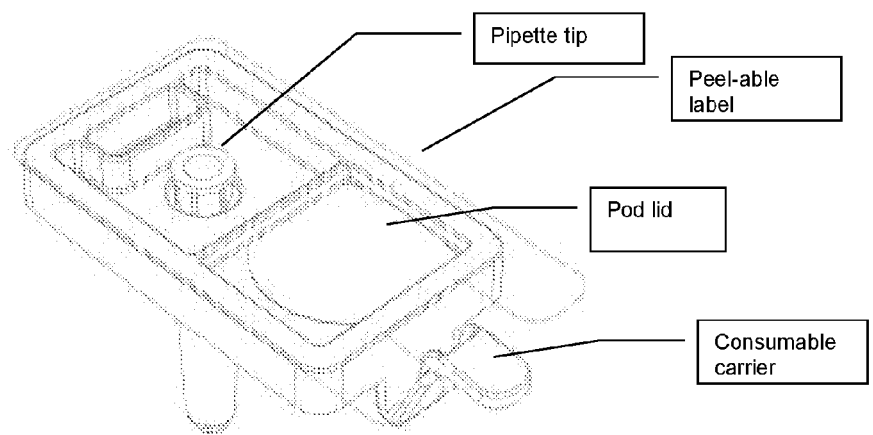
Figure 14 Illustration of the consumable cartridge

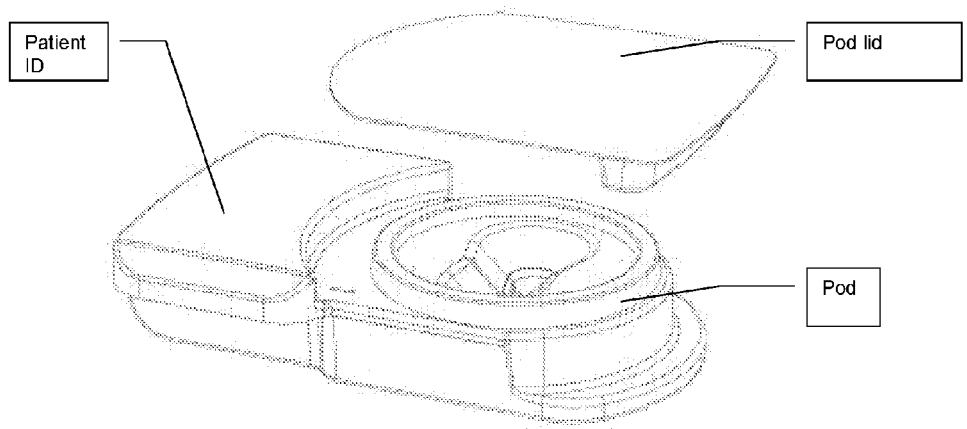
Figure 15 Illustration of the pod and lid
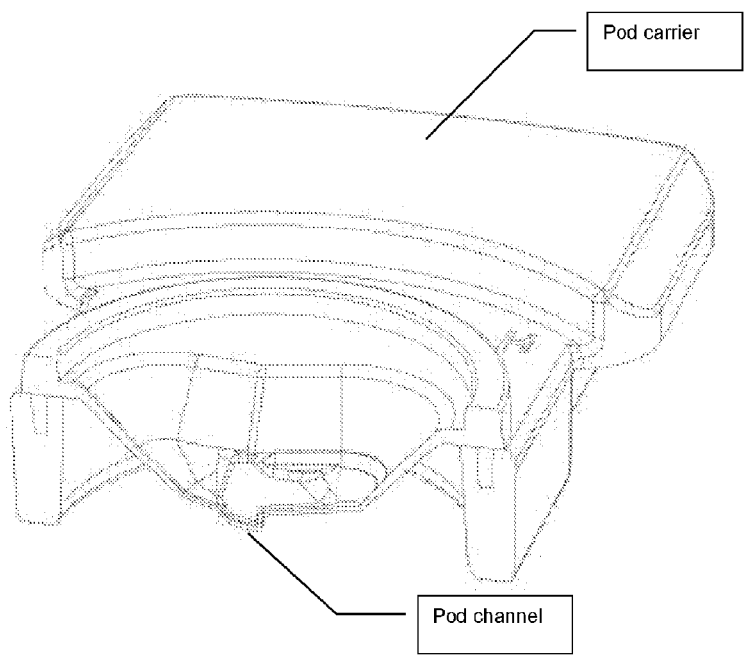
Figure 16 Illustration of a cross section XX of pod

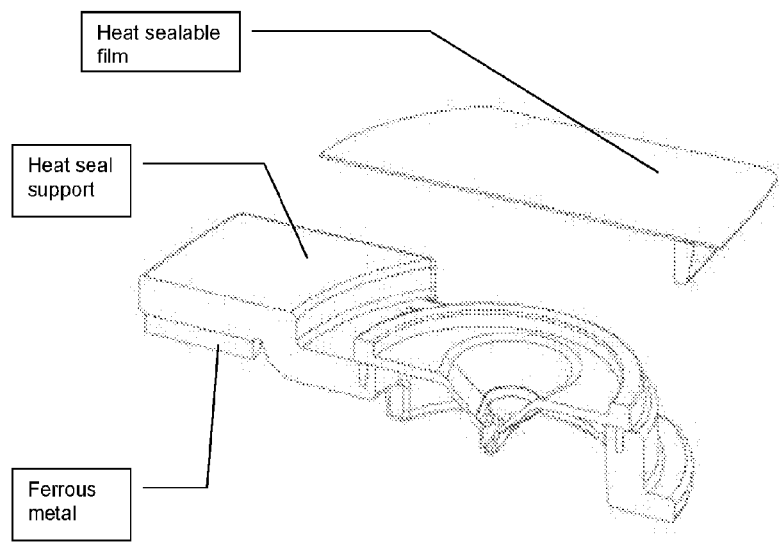
Figure 17 Illustration of the cross section YY of pod
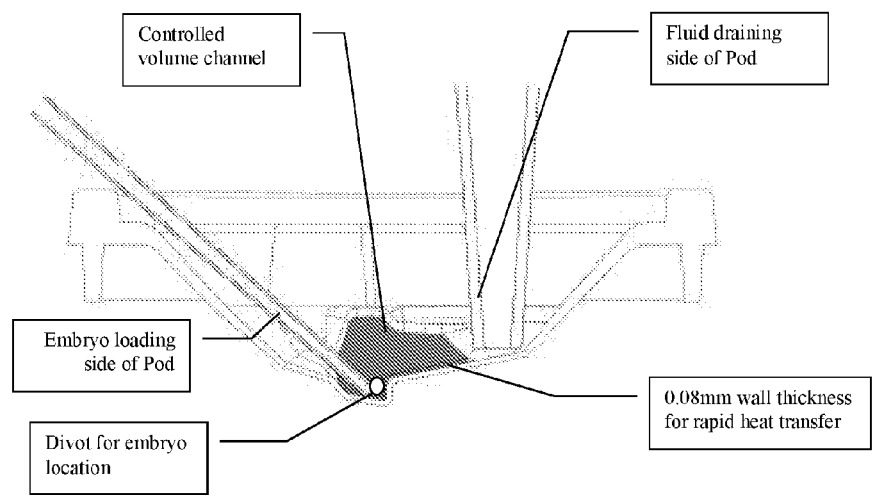
Figure 18 Illustration of the cross section on pod and controlled volume channel

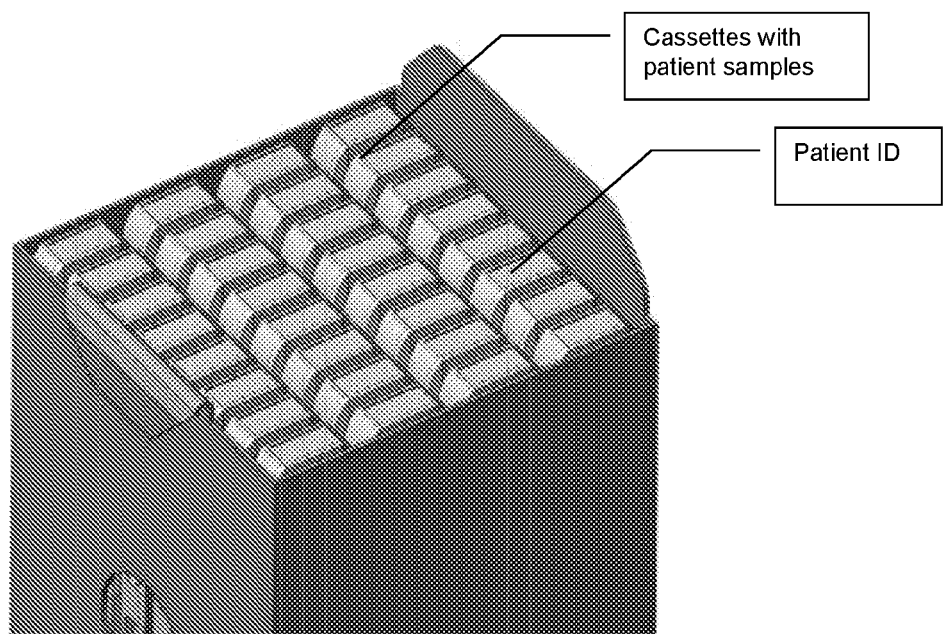
Figure 19 Example of a canisters with all the cassettes loaded

METHOD, SYSTEM AND APPARATUS FOR IMPROVED MICROMANIPULATION AND STORAGE

RELATED APPLICATIONS

This application claims priority to Australian Provisional Patent Application No. 2013900039 in the name of Genea Ltd, which was filed on 7 Jan. 2013, entitled "Method, System and Apparatus for Improved Micromanipulation and Storage" and the specification thereof is incorporated herein by reference in its entirety and for all purposes.

FIELD OF INVENTION

The present invention relates to the field of manipulation and handling of biological materials. In particular, this invention relates to apparatus and methods for the micromanipulation of biological materials, for example, apparatus and methodologies for use in the cryopreservation of biological materials including human and non-human oocytes, embryos and blastocyst, gamete and stem cells. Whilst the invention has been developed and has application in a wide range of micromanipulation situations and techniques with a range of biological materials, it finds particular application for use in the cryopreservation of human oocytes, embryos and stem cells by vitrification as applied during In Vitro Fertilisation (IVF) procedures and the like. However, the invention is not limited to that use, only.

BACKGROUND ART

Throughout this specification the use of the word "inventor" in singular form may be taken as reference to one (singular) inventor or more than one (plural) inventor of the present invention.

It is to be appreciated that any discussion of documents, devices, acts or knowledge in this specification is included to explain the context of the present invention. Further, the discussion throughout this specification comes about due to the realisation of the inventor and/or the identification of certain related art problems by the inventor. Moreover, any discussion of material such as documents, devices, acts or knowledge in this specification is included to explain the context of the invention in terms of the inventor's knowledge and experience and, accordingly, any such discussion should not be taken as an admission that any of the material forms part of the prior art base or the common general knowledge in the relevant art in Australia, or elsewhere, on or before the priority date of the disclosure and claims herein.

The technologies involved in and applied for cryopreserving of human and animal embryos are well established and with the application of suitable skill and know-how, the current technologies have achieved great improvement in the reliability and success for In Vitro Fertilisation procedures. For the purposes of this description, the following terms are taken to have the following definitions, with respect to the handling of embryos:

"Freezing" is the cooling of a liquid to a solid state which may include crystallisation.

"Vitrification" is the cooling of a liquid to a solid state without crystallisation.

"Cryopreservation" is a process where the cells are preserved by cooling to sub-zero temperature, typically −196 C.

"Thawing" is the process of changing from a frozen solid state to a liquid by gradual increase in temperature. This is most commonly associated with oocytes/embryos that have been cryopreserved by slow freezing techniques.

"Warming" is the process of changing from a vitrified solid state to a liquid state by rapid increases in temperature that prevents crystallisation. This is most commonly associates with oocytes/embryos that have been cryopreserved by vitrification techniques.

The techniques as understood and applied involve harvesting and cryopreservation of embryos, with a plurality of steps involving harvesting and extraction of oocytes, in vitro fertilisation thereof and the subsequent cryopreservation and storing of such fertilised eggs and the resultant embryos and/or late stage blastocysts. The multitude of steps and handling stages required are heavily reliant on a high level of know-how and skill via the technical operators. The embryos or blastocysts once frozen, are then made available as required and can be thawed and transferred to the recipient whereby successful implantation to the uterus can result in normal development of a foetus and a resultant pregnancy.

More recently, such cryopreservation techniques have been successfully applied to unfertilised eggs and oocytes. Oocyte cryopreservation involves harvesting, freezing and storing of eggs or oocytes from a donor female in an unfertilised state. Such frozen eggs can then be drawn from a storage bank, thawed and made available for fertilisation and transferred to a donor on demand.

The techniques of cryopreservation as applied to oocytes rather than fertilised eggs and embryos, has certain ethical and medical advantages and has been subject to increased research and experimentation to improve the techniques involved.

The process of cryopreservation, particularly when applied to "live" biological materials, involves a high degree of trauma for the biological material in question, particularly having regard to the multiple handling steps required in accordance with current techniques. In addition to the trauma experienced as a result of physical handling, the biological material is also subject to potential ice crystal formation during any freezing process, in addition to osmotic shock and toxic shock experienced during movement through a plurality of processing chemical solutions.

The traditional method of preparing frozen biological material includes the slow cooling of the material and its surrounding solution down to the storage temperature, with a view to deliberately initiating the formation of ice crystals remotely from the biological material per se. The traditional method is not optimal due to continuous formation of ice crystals. Alternative "vitrification" methods have been developed to address the ice crystal formation issues, however vitrification requires considerable technical skill for successful execution. Vitrification involves the transformation of the processing solution into a glass-like amorphous solid that is free from any crystalline structure, followed by extremely rapid cooling. The extremely rapid cooling is what enables the solution to achieve the glass-like amorphous state.

The application of either the traditional method of freezing or vitrification involves the use of chemical compounds and solutions, which are added to the biological material to minimise cell damage during the freezing processes. The chemical compounds and solutions are known as cryoprotectants and include permeating and non-permeating solutions. Permeating cryoprotectants are small molecules that readily permeate the membranes of the biological material with the formation of hydrogen bonds to the water molecules of the biological material with the aim of preventing ice crystallisation thereof. Examples of such permeating cryoprotectants are Ethylene Glycol (EG), Dimethyl Sulphoxide (DMSO) and Glycerol. At low concentrations in water, such permeating cryoprotectants lower the freezing temperature of the resultant solution and can assist in the prevention and minimisation of ice crystallisation. At higher concentrations which may differ at different cooling rates, such permeating cryoprotectants inhibit the formation of typical ice crystals and can lead to the development of a solid glass-like or vitrified state in which water is solidified prior to crystallisation or expansion. Toxicity of such permeating cryoprotectants increases with their increasing concentrations and is potentially toxic to the biological material in question and accordingly, the biological material must have minimal exposure to the permeating cryoprotectants over a very short period of time, or alternatively, exposure at a low temperature, whereby the metabolic rate of the biological material in question is reduced.

In contrast to the permeating cryoprotectants, the non-permeating cryoprotectants remain extracellular. Some examples of non-permeating cryoprotectants include disaccharides, trehalose and sucrose. The disaccharide cryoprotectants act by drawing free water from within the biological material and dehydrating the intracellular spaces. The resultant dehydration allows them to be used in combination with permeating cryoprotectants, such that the net concentration of the permeating cryoprotectant can be increased in the intracellular space. These techniques further assist the permeating cryoprotectant in preventing or minimising ice crystal formation.

During the vitrification process, permeating cryoprotectants may be added at a high concentration while the biological material's temperature is controlled at a predetermined level above freezing. However, because the toxicity of such high concentrations of permeating cryoprotectant can be substantial, it is not possible to retain the biological material at such temperatures for extended periods. Alternatively, a reduced time can be allowed for equilibrium after which the biological material, which may include oocytes or embryos are plunged directly into liquid nitrogen (where liquid nitrogen is hereinafter referred to as "$LN_2$") to effect freezing. The extremely rapid rate of cooling, minimises the negative effects of the cryoprotectant on the biological material and also, minimises ice crystal formation by encouraging vitrification.

The vitrification process involves exposing the biological material to a number of vitrification solutions. The vitrification solutions are typically added to successive wells in a multi-well culture dish, where the dish and solutions are warmed to a predetermined temperature, determined in accordance with the requirements of the biological material in question.

In a conventional protocol, the biological material is physically transferred to a first solution in a first well and then washed by physically moving the biological material or cell through the solution in question with a cell pipetting device. The washing process is repeated in a second, third and fourth well over predetermined periods of time until the biological material or cell is considered ready for cryopreservation. The biological material is then physically drawn up with a predetermined amount of vitrification solution using a pipette or other handling device. A droplet containing the biological material or cell to be vitrified is then pipetted onto the vitrification device. The vitrification device is then physically transferred with the droplet and biological material attached and directly plunged or sealed into a container that is plunged into $LN_2$ or placed onto the surface of a vitrification block that has been pre-cooled with $LN_2$. Once the biological material and the carrying fluid has become vitrified, the vitrification device is then inserted into a pre-chilled straw or other storage device, located in a slot in the vitrification block for subsequent transfer to long-term cold storage in either $LN_2$ or $LN_2$ vapour.

Various vitrification devices are used to manipulate the sample during the cryopreservation processes. Some propose a pipette style device in which the sample is sucked into a hollow tube which is then plunged directly into the solution or $LN_2$. Such device is marketed by Irvine Scientific and sold as Cryotip®.

Other techniques use a loop/hook style device which will have a closed loop or an open hook made from plastic or metal wire attached to the end of a stem and is used to carry the biological sample. Such devices are marketed by Cryologic under the trade name of fibreplug™ or Cryoloop™ as defined in published international patent application WO00/21365.

Other tools are utilised as disclosed in international application WO 02/085110 "Cryotop" which is a flexible strip attached to a piece of plastic. In which the sample is placed on the strip and plunged directly into $LN_2$.

Current prior art requires many embryo handling steps using multiple apparatus where every handling step increases the chance of losing the embryo. It is estimated that 1-2% of embryos lost are attributed to handling errors during the vitrification step.

The trauma associated with the previously described processes and in particular the trauma imposed by repeated physical handling and manipulation of extremely delicate biological material including eggs, cells, embryos and blastocysts, impacts on the survival rate and hence the success of the processes and methods previously described. Furthermore, the physical dynamics of a living embryo responding to osmolality changes introduce rapid shrinkage and expansion and other changes to the shape of the embryo which further challenge any handling, and in particular, automated handling of such biological materials. Any automation needs to manage such dynamics as well as manage a range of different embryo types, fluid movements along with a high range of fluid viscosities. Clearly, in order to maximise the chances of success and minimise trauma imposed on the materials being handled, it is highly desirable to reduce the physical handling of such delicate materials to an absolute minimum, which should mitigate cell shrinkage and expansion.

As noted above, the vitrification process involves exposing an embryo, or cell, to increasing concentrations of cryoprotectant solutions (also referred to as equilibration and vitrification solutions) so that water inside the cell is gradually removed and replaced. The concentrations of the fluids, the pace of fluid concentration changes that the cell experiences, the temperature at which the process takes place and the time over which it takes place are all important variables to achieve embryo viability in the end. Also important are the heat transfer rates, both the cooling during vitrification and warming to retrieve the embryo. Finally the addition of 'warming' solutions allows the cryoprotectants now inside the cell to be removed and replaced by water to ideally return the embryo to its initial state.

In addition to the above discussion there are a number of drawbacks with prior art, which can be summarised as follows: It is a very difficult and time consuming process which requires very skilled operator(s). Embryo loss is solely dependent on the skill of the operator. Variation in skills means variation in results in both embryo recovery (where an embryo is simply not found) and embryo survivability (embryo did not survive). Variation between lab environment, ie some labs might be running at 20° C. whilst others will be at 30° C. introduces problems. It is known that temperature variations or given temperature conditions can accelerate or decrease the biological reaction of the embryo. Over-exposing or under-exposing may damage the embryo. Variation in the processing time by humans means some embryos get over-exposed whilst others get under-exposed, ie overexposing the embryo in the final solution by 30 seconds may damage the embryo. Current consumables adapted for closed vitrification are heat sealed and therefore require cutting to retrieve the sample. The difficult and time consuming step of taking too long to retrieve the sample will damage the embryo ie more than 20 seconds. In practice moving embryos to increasing concentrations of cryoprotectant solutions is performed in a minimum amount of steps, usually 2-3, and this exposes cells to osmotic shock associated with considerable shrinking and subsequent expansion of cells, with the associated stress it causes on cell membranes and cytoskeleton.

Accordingly, variability may be one of the major issues with the current prior art systems. Vitrification variability can occur in the following areas:

Type of vitrification device being used. Currently there are over 15 types on the market.
The media being used. Currently there are over 10 media suppliers.
Embryologist skills and experience
Protocol (step time, temperature, cooling rate, warming rate, media volume)
Environment (temperature, humidity)

Due to the variability in the environment, human involvement and protocols has greatly contributed to the lack of consistency in cryopreservation of biological material and the resultant low pregnancy rates.

It is therefore desirable to eliminate the variability by providing an automated system to control the environment and ensure a repeatable cryopreservation of biological materials.

There are 3 types of vitrification devices "closed" system, "semi closed" and "open" system. A "closed" system refers to a vitrification system that prevents direct contact between $LN_2$ and the biological material. Cryotip® is considered to be a "closed" system. An "Open" system refers to a vitrification system that allows direct contact between $LN_2$ and the biological material. Fibreplug™, Cryoloop™, and Cryotop® are all considered to be an "open" system. The problem with open systems is the direct contact with the requisite $LN_2$ cooling solution with the risk of pathogen transmission to the biological sample at the time of freezing or during the storage. As the biological material is in contract with the $LN_2$, contamination of sample can occur if the $LN_2$ is contaminated or the $LN_2$ can be contaminated if the sample is contaminated. Many countries have banned open systems due to the high risk of sample contamination.

Example of Cryotip® Protocol.

In the particular example of the Cryotip® system, there are a number of risky process steps that vary from low to medium to high risk in nature. For example, in the vitrification stages there is included the steps of introducing equilibration medium then vitrification medium then the loading and vitrification, which generally takes an estimated time of about 16 minutes. As a starting protocol for this stage embryos are transferred usually at a maximum of two at a time from culture dish to the equilibrium solution (ES) drop with a timer starting. Then for equilibrium media, the embryo is incubated undisturbed for about 6-10 minutes and 2 minutes prior to completion of this, four 20 µL drops of vitrification solution (VS1-4) are dispensed in a row. By the end of the equilibration time the embryos are transferred to a vitrification solution (VS), loaded, sealed and plunged within 90 seconds by transferring the embryos with minimal volume of medium from ES to VS1 for 5 seconds, then transfer to VS2 for 5 seconds then transfer to VS3 for 10 seconds. The high risk steps then occur with the loading and vitrification proper in which it is required to aseptically attach the wide end of a Cryotip® device to an aspiration tool, such as a luer syringe, using the Cryotip® connector. When the specimens are ready to load into the Cryotip® the metal cover sleeve is aseptically slid carefully along the straw to expose the fine tip end. The specimens are then gently loaded into the Cryotip® between its $2^{nd}$ and $3^{rd}$ mark by aspiration using the plunger on the syringe to control the uptake of medium and specimens being careful not to fill oocytes or embryos above the $3^{rd}$ marker. Then the fine tip is heat sealed below the $1^{st}$ mark then sliding the metal cover sleeve down over the fine tip to protect it. The connector and syringe are then removed and the wide end of the Cryotip® is heat sealed above the $4^{th}$ mark. Finally the sealed Cryotip® is plunged with the metal covered side down first into the $LN_2$ reservoir.

SUMMARY OF INVENTION

It is an object of the embodiments described herein to overcome or alleviate at least one of the above noted drawbacks of related art or prior art systems or to at least provide a useful alternative to prior art systems.

In a first aspect of embodiments described herein there is provided apparatus for micromanipulation of biological material, said apparatus comprising a vessel having a reservoir wherein said vessel has a channel formed in a portion of said reservoir, said channel comprising an intermediate restriction dimensioned to resist passage of said biological material but allow passage of liquid treatment solutions wherein the channel comprises walls of a thickness in the range of about 0.01 mm to about 0.90 mm.

The channel further may comprise a divot having a volume of between about 0.04 µl to about 0.30 µl adapted for retaining and/or positioning an embryo therein within at least a modicum of solution.

The surface of the channel exposed to biological material and liquid treatment solutions is preferably surface treated to allow fluid to wet and spread out upon the surface of the channel. Further, the channel walls may comprise polymer material and the apparatus is formed by injection compression moulding comprising a two part construction. The polymer may comprise polypropylene.

The two part construction may comprise a first mould injection of polymer material and a second mould injection of polymer material. One of the first or second mould injections may comprises the formation of the channel.

Alternatively, the two part construction may comprises two separately formed portions of the apparatus.

Preferably, the wall thickness is about 0.08 mm-0.12 mm. At this range it has been found by the inventor to promote fast heat transfer and thick enough to prevent gas and liquid transfer.

Preferably, the surface treatment comprises one or a combination of the following methods: plasma surface treatment, corona treatment, sterilisation, flame treatment or chemical treatment.

In another aspect of the invention and its embodiments there is provided apparatus for micromanipulation of biological material, said apparatus comprising a channel for accommodating said biological material and allowing passage of liquid treatment solutions, the apparatus comprising a two part construction and wherein two portions of the apparatus are adapted to be heat sealed with a secondary material intermediate the two portions prior to a vitrification process step.

Again the two part construction may comprise a first mould injection of polymer material and a second mould injection of polymer material. One of the first or second mould injections may also comprises the formation of the channel.

Also, again alternatively, the two part construction may comprise two separately formed portions of the apparatus.

In yet another aspect of embodiments described herein there is provided apparatus for micromanipulation of biological material, said apparatus comprising a channel for accommodating said biological material and allowing passage of liquid treatment solutions, the apparatus comprising a two part construction wherein the two parts are adapted to be heat sealed with a secondary material intermediate the two parts prior to a vitrification process step.

Preferably, in the above noted apparatus, the secondary material allows for peeling separation of the two part construction.

The apparatus may comprise one of a pod for accommodating said biological material or a pipette for transferring said biological material.

The apparatus is preferably adapted for one or a combination of positioning, connecting, locating or providing thermal contact by operative association with an arrangement of magnets. The magnets are located in a pre-existing structure into which the apparatus is adapted for insertion or movement. The pre-existing structure comprises one or a combination of a cassette, a cartridge or canister. Furthermore, the apparatus of preferred embodiments is adapted for floating in a $LN_2$ bath.

Again, preferably, the two part construction comprises polymer material. The two parts comprise polypropylene and the secondary material is a laminate adapted to prevent ingress of $LN_2$ to the apparatus.

In yet a further aspect of embodiments described herein there is provided a system for vitrification of a biological specimen comprising one or combination of:

a software operable means for controlling the temperature environment;

a software operable means for controlling fluid dispense volume and velocity and aspiration volume and velocity for the application of liquid treatment solutions to the biological specimen, and;

a software operable means for controlling protocol time.

The system may be configured wherein the temperature is controlled in a range of about 5° C. to about 40° C. Further, the temperature is preferably controlled in a range of about 19° C. to about 37° C.

The fluid dispense and aspiration volume may be controlled to a range of about 0.1 µl to about 15 µl with an accuracy of about 1 µl±0.2 µl to about 10 µl±1 µl.

The fluid dispense and aspiration velocity may be controlled in a range from about 0.01 µl/s to about 5 µl/s.

In yet a further aspect of embodiments there is provided a system for micromanipulation of biological material comprising one or a combination of independent single axis robot arms where each single axis robot arm is mounted to a static assembly wherein a combination of robot arms provides a global coordinate system for movement in at least two degrees of freedom, said system being adapted for handling an apparatus as described herein through at least two or a combination of the following process steps:

embryo loading;
equilibration;
heat sealing;
vitrification.

In still a further aspect of embodiments, there is provided a method of micromanipulation of biological material utilising apparatus as described herein, the method comprising the steps of:

loading at least one embryo into the apparatus in a buffer solution;

replacing the buffer solution with an equilibration solution at a predetermined flow rate;

equilibrating the loaded embryo in the equilibrating solution for a predetermined equilibration time period;

replacing the equilibrating solution with a vitrification solution at a predetermined flow rate;

heat sealing the apparatus;

plunging the apparatus into a liquid cooling bath.

The step of heat sealing noted above may be performed with a precondition of optical detection of the presence of a consumable for containing biological material loaded in the apparatus.

Preferably, the steps are performed by one or a combination of independent single axis robot arms where each single axis robot arm is mounted to a static assembly wherein a combination of robot arms provides a global coordinate system for movement in at least two degrees of freedom.

Other embodiments of the present invention may comprise apparatus adapted to micromanipulate biological material, said apparatus including: processor means adapted to operate in accordance with a predetermined instruction set, said apparatus, in conjunction with said instruction set, being adapted to control the timing, temperature dispensing volumes and flow velocity involved in performing the method steps as disclosed herein. The predetermined instruction set preferably comprises computer software adapted for controlling fluid exchange in the apparatus to allow for a gradual increase in the concentration of the vitrification solution so as to decrease an osmotic shock to the embryo and increase cryopreservation quality. The liquid cooling bath disclosed in methods herein preferably comprises $LN_2$ and the apparatus, in conjunction with said instruction set, may be adapted for automating transfer of $LN_2$ to and from the liquid cooling bath.

Other embodiments comprise a computer program product including: a computer usable medium having computer readable program code and computer readable system code embodied on said medium for micromanipulation of biological material within a data processing system, said computer program product including: computer readable code within said computer usable medium for performing the method steps as disclosed herein. The computer readable code preferably comprises computer software adapted for controlling fluid exchange in the apparatus to allow for a gradual increase in the concentration of the vitrification solution so as to decrease an osmotic shock to the embryo and increase cryopreservation quality It is to be noted for the purposes of this description herein that the term "consumables" is used as reference to pods, pipettes, media vials or other consumable apparatus that may be used in the system and apparatus for micromanipulation or vitrification of biological specimens such as embryos.

Other aspects and preferred forms are disclosed in the specification and/or defined in the appended claims, forming a part of the description of the invention.

In essence, embodiments of the present invention stem from the realization that that the process of vitrification remains un-automated. Current methods require the embryologist to conduct multiple transfer of the oocytes/embryo through varying media using a pipette in a manual fashion. Once the embryo is processed the embryo is then moved to a plastic device to reduce the thermal mass to allow for fast cooling and storage. The vitrification process is time consuming, tedious and fiddly. More significantly the output quality is highly dependent on the skill of the technician. Embodiments of the present invention allow vitrification to be automated by integrating the processing of the embryo and the freezing/storage into the same device. In one particular embodiment, a device has been developed which allows media to be exchanged whilst culturing the embryo without pipette transfer. As the device has very little thermal mass, the device lends itself to be used as the freezing/storage device. Further to this, embodiments of the present invention provide a proprietary consumable and an instrument workstation.

Advantages provided by the present invention comprise the following:
- Modified pipettes and control mechanisms of preferred embodiments deliver smaller tolerance volumes that provide greater control over a vitrification process;
- Heat sealing to avoid damaging embryos;
- Heat sealing tubes are selectively activated based on optical detection to only act on occupied cassette;
- Overall configuration of machine allows for separation of sealing mechanisms from solution exchange mechanisms;
- Use of a heavy duty laminate material that seals against vitrification storage to give strong peelable seal. In this respect, no other vitrification storage device uses a secondary seal. They are usually sealed against each other and therefore requires cutting to open. The laminate can be sealed to polypropylene material;
- The seal prevents ingress of $LN_2$ inside;
- The seal integrity is maintained in $LN_2$ temperatures;
- The instrument of preferred embodiments can provide a controlled environment to ensure consistent embryo processing every time;
- Processing of multiple vitrification devices at the same time;
- One to many devices at a single go.

Further scope of applicability of embodiments of the present invention will become apparent from the detailed description given hereinafter. However, it should be understood that the detailed description and specific examples, while indicating preferred embodiments of the invention, are given by way of illustration only, since various changes and modifications within the spirit and scope of the disclosure herein will become apparent to those skilled in the art from this detailed description.

BRIEF DESCRIPTION OF THE DRAWINGS

Further disclosure, objects, advantages and aspects of preferred and other embodiments of the present invention may be better understood by those skilled in the relevant art by reference to the following description of embodiments taken in conjunction with the accompanying drawings, which are given by way of illustration only, and thus are not limitative of the disclosure herein, and in which:

FIG. 1 illustrates some typical process steps in accordance with a workflow of a preferred embodiment of an automated vitrification instrument according to the present invention;

FIG. 2 diagrammatically illustrates an instrument layout in accordance with a preferred embodiment;

FIG. 3 is a chart illustrating a breakdown of each of the components of an instrument in accordance with the present invention;

FIG. 4 shows an exemplary instrument in accordance with a preferred embodiment of the present invention with covers in place;

FIG. 5 shows the principle module of an instrument in accordance with a preferred embodiment of the present invention;

FIG. 6 shows a pipette module in accordance with an embodiment of the present invention;

FIG. 7 shows a heat sealer and lid transfer module in accordance with an embodiment of the present invention;

FIG. 8 shows a transverse axis assembly used in an instrument in accordance with a preferred embodiment of the present invention;

FIG. 9 shows an exemplary $LN_2$ transfer bucket used in embodiments of the present invention;

FIG. 10 illustrates an exemplary user interface display in accordance with a preferred embodiment of the present invention;

FIG. 11 shows an example tray in operation with consumables and media loaded thereon in accordance with an embodiment of the present invention;

FIG. 12 shows an example of a cassette with pods loaded in accordance with an embodiment of the present invention;

FIG. 13 shows an example media cartridge in accordance with embodiments of the present invention;

FIG. 14 shows an example of a consumable cartridge used in preferred embodiments of the present invention;

FIG. 15 shows a pod and lid in accordance with a preferred embodiment of the present invention;

FIG. 16 is a cross section in perspective view of the pod of FIG. 15;

FIG. 17 is a further cross section in perspective view of the pod of FIG. 15;

FIG. 18 is a cross sectional illustration of the pod of FIG. 15 and a controlled volume channel of a preferred embodiment of the present invention;

FIG. 19 shows an example of a canister in accordance with an embodiment of the present invention with all the cassettes loaded.

DETAILED DESCRIPTION

For the purposes of this description, the following definitions apply. The term "embryo" in this document refers to an embryo, mammalian or non-mammalian, which includes but is not limited to a human embryo at stages commonly occurring during the period when the embryos can be kept in in vitro conditions in the laboratory, commonly days 1 to 6 from oocyte retrieval. The term "embryo", implies also the "oocyte", unless otherwise specified, where an oocyte is taken to be an unfertilised metaphase II stage 1-cell egg before fertilization or an immature GV stage oocyte before final oocyte maturation. "Solution" relates to fluid used for the purpose of cryopreservation of an embryo. The term "consumable" refers to disposable low cost devices designed for accommodating and handling the embryo or oocyte for introduction and preparation for vitrification as handled by a user or technician and interfaces to laboratory instrumentation. A "cassette" may be the holder/platform in which multiple consumables are contained during the vitrification process, and which also serves as the long term storage platform. A "cartridge" refers to a container designed to contain vitrification solutions, waste, lids and/or tips needed for vitrification process and, a cartridge can be designed to be either single use per process or single use per consumable. A "protocol" is taken to be the sequence of solution exchanges, including their timing, velocity, temperature and volumes, that prepare an embryo for the final vitrification step by plunging into $LN_2$. "Recovery" refers to a stage where an embryo that has undergone the complete vitrification and warming process is located and collected, ready to be processed further. "Survival" is reference to an embryo that has undergone the complete vitrification and warming process and has been recovered, shows clear signs of cellular and developmental viability after a period in culture that is equivalent or less than currently used for embryos after cryopreservation and warming. More specifically, for the purposes of this description, survival means that the embryo is judged clinically suitable for subsequent clinical processes (such as fertilisation for oocytes, embryo transfer for embryos).

In preferred embodiments an instrument and apparatus is provided to automate the vitrification preparation process. The actual vitrification step, where the embryo and surrounding fluid enter a vitrified state, may also be automated. Further a consumable is provided which will allow for the vitrification process to take place without a need to move the embryo once placed into it, and also allows warming procedures to take place manually, without compromising embryo viability.

On average, a medium size IVF clinic may freeze approximately 800 embryos or less each year. A large IVF clinic may freeze up to about 4000 embryos or oocytes each year. Currently the process includes time critical steps and/or procedures and protocols that require fine motor skill control. The intended user interaction for this is described hereinbelow.

A key driver is to keep the instrument simple. As such, the instrument utilises an X-axis to move embryo pods (pods) from the loading area to the various positions within the instrument such as the dispense position or sealing position. The other functions move toward a gantry carriage in the Z-direction.

In one preferred aspect, embodiments of the invention provide a controlled volume channel which comprises a divot for retaining and/or positioning the embryo for processing. In doing so, the divot is provided with a controlled divot volume, preferably in the range of about 0.04 µl to about 0.30 µl, which will be sufficient to accommodate at least a modicum or limited amount of solution in the embryo can be disposed. This serves to prevent embryos from drying. It also controls the carryover of previous solutions throughout processing. The divot assists with initial positioning of the embryo and provides for retention of the embryo during fluid exchange. Furthermore, the channel comprises walls of a thickness in the range of about 0.01 mm to about 0.90 mm and preferably of about 0.08 mm for enabling rapid heat transfer to occur within the pod.

A central function of the instrument is to complete the vitrification preparation process, and potentially also to facilitate the vitrification of the embryo. To achieve that, the main steps to be completed by the instrument in a typical protocol are represented in FIG. 1. The instrument may also complete other functions such as maintaining the pod and solution temperatures throughout the process. The instrument, in preferred embodiments, will perform accurate fluid exchange with the pod. Nominally this would be via standard OEM pipette tips. The instrument may also seal the pod so that the system becomes a 'closed' system in regard to possible $LN_2$ contamination. A typical instrument preparation process involves a user performing the following steps:

User start the instrument and select protocol
Fill the $LN_2$ bucket and load into instrument
Load the media cartridge and consumable cartridge in the appropriate row into the operating tray.
(Ideally) Pre-warm Operating Tray to expected protocol temperature
Putting the embryo and 2-8 µl of suitable buffer solution, eg Cryobase®, into appropriate pods and place (if not already placed) in Cassette
Load Operating Tray into Instrument
Load Cassette into Instrument
Press Start The typical Instrument unloading process involves the steps of:

Attending the instrument when it sounds a warning alarm
Removing, or opening, the lid from the $LN_2$ bucket
When the 'Unload Cassette' alarm sounds, promptly opening the access door and removing the Cassette
Promptly dunking the Cassette in $LN_2$.
The $LN_2$ bucket is then removed from the instrument to transfer the Cassette to long-term storage.

Logged data can be accessed via a SD card, or its equivalent, that may capture relevant information to assess correct processing at a later date when investigating possible causes of embryo warm and viability results. It is envisaged that service personnel will be able to connect to the instrument via an external connection and PC. This will most likely be via RS232 or RS485 interfaces and there may be limited debug functionality made available via a GUI as would be appreciated by the person skilled in the art.

With reference to FIG. 5, in a preferred embodiment the automated instrument employs a single X-axis to move an Operating Tray accommodating the embryos between a Solution Exchange Robot, a Lid Transfer Robot and Heat Sealers. The X-axis moves the Operating Tray to the location required for each of the functions to be performed with independent Z-direction movement only.

There have been three basic options considered for detection of the loaded consumables, namely, physically switched, optically switched and image detection. An anticipated typical workflow for the Consumable Detection is as follows:

Image Detection
  Trigger for detection (whether it is a door sensor or a user screen input)
  Capture image of consumable tray
  Perform image analysis/detection algorithm to detect components
  Check that components are loaded in an allowed state
  If ok, continue or, if not ok, provide feedback to user to correct
Optical Switched Detection
  Trigger for detection (whether it is a door sensor or a user screen input)
  Perform optical check on pod, media cartridge, tip and lid.
  Check that components are loaded in an allowed state
  If ok, continue or, if not ok, provide feedback to user to correct A number of key features and design considerations have been taken into account for the detection of consumables such as, for example, Adequate resolution (and colour if applicable) to detect pods, Cartridges, and components (vials, tips, lids)

Detection of presence of the above-listed parts

Detection of correct orientation of the above-listed parts

Lighting condition control to allow a 'reasonable' detection algorithm to work in typical laboratory lighting (may not require it to be robust in extreme conditions)

LED brightness control

Controlled effect of external lighting (eg tinted covers)

Solution exchange is an important consideration and has been contemplated as follows. To equilibrate the embryos, the instrument needs to dispense accurately into the pod and also remove solution. The Solution Exchange system is provided to allow dispense tips to be positioned correctly in each of up to four pod consumables and to perform the fluid exchanges necessary for the equilibration of the embryos prior to vitrification. Fluid dispense velocities are considered an important factor in the present invention and preferred embodiments provide an instrument with the ability to have variable dispense and aspiration velocities to accommodate oocytes and a range of embryo types. This functionality of variable dispense velocities correlates with variable equilibration protocols to provide for controllable equilibration sequences.

The system may use features on the pods to guide the tip to correct placement. An anticipated typical workflow for the automated vitrification is Instrument check to ensure pod, consumable cartridge and media cartridge are correctly position Fit new sterile disposable tips to the fluidics system Aspirate Buffer Solution from the pod, leaving just the required volume of about 0.1 µL protecting the embryo in the formed divot, from desired location Dispense drained solution into a waste container Aspirate Equilibration Solution 3 (ES3)

Slowly dispense about 5 µL of Equilibration Solution 3 into pod at desired location(s) at a dispense velocity of 0.1-3.0 ul per sec Wait required protocol time (4-20 minutes)

Slowly drain Equilibration Solution 3 from the pod, leaving just the about 0.1 µL protecting the embryo in the divot, from desired location Dispense drained solution into a waste container or desired waste position Collect Vitrification Solution 4 (VS4)

Dispense about 1 µL of Vitrification Solution 4 into pod at desired location(s)

Wait required protocol time (30-120 sec)

Eject tips from system

Pick up lid and place over the pod

Heat seal the lid onto the pod

Manually or automatically remove the cassette and place into $LN_2$

Place the cassette into cryostorage tank

Instrument Will

Maintain sterility of solutions entering the pod

Prevent any cross-contamination between embryos in the same run or subsequent runs Drain the pod of approximately 2 ul-8 ul (or up to about 10 µL) of Buffer Solution and again of VS3

Dispense about 5 µL±15% ES3

Dispense about 1 µL±20% VS4 Aspirate and dispense velocity to be controlled at 0.01 ul-2 ul per second Controlled the processing temperature to a predetermined temperature.

Temperature to be from about 19 to about 37 degrees.

Use of a new disposable sterile tip for each pod

Fluidics interface from the pump to a disposable tip, and the disposable tip to the pod is a consideration. This interface should be reliable and allow for differences in tip push-on height, and tip runout tolerances (up to about 1.016 mm)

Fluidics mechanism is adapted to interface to the electronic control system

Fluidic dispenser is adapted to mount to a Tip positioning system

Another advantage of the instrument and pod design is the software can control the fluid exchange to gradually increase the concentration of the vitrification media, which in turn will decrease the osmotic shock to the embryo and increase cryopreservation quality.

To perform the solution exchange steps, the instrument has been adapted to pick up tips and after the last solution exchange is performed, it will eject the tips.

In one embodiment, the automated system implements a bent stainless steel profile that engages the pipettes above the tip so that a vertically upwards move by the pipette axis would disengage the tips into a container below. This form of removal performs reliably. Moreover, the usability of tip removal should be carefully considered in embodiments of the invention to ensure it is user friendly and safe such that the system makes it not easy for a user to come into contact with the contaminated tips or solutions. With this in mind, embodiments have interfaces with specifications that provide the following:

One tip per pipette per run

Tips are typically pushed on with a force of about 10N per tip

Tips are typically removed with less force than required to push them on

Tips should be ejected into a easily removable container with a closed bottom and side (can be open top) for easy and safe tip disposal In a preferred embodiment, the consumable is heat-sealed to achieve a sealed vessel that will prevent direct contact between $LN_2$ and the embryo or vitrified fluid. In particular, a preferred embodiment provides transfer of a lid and heat sealing of the lid to a pod to prevent $LN_2$ contacting the embryo or vitrification fluid during vitrification and storage. FIG. 7 shows a heat sealing system on a preferred form of instrument in accordance with the present invention comprising a single axis, for combined lid transfer and heat sealing Mechanical sealing has non-mitigated technical risks including providing substantial imperviousness, the rapid freezing of stressed features required to achieve a mechanical seal, and then there are also concerns about those features again during the warming process. Additionally, the allowable space(s) for features to facilitate mechanical sealing significantly limit the heat transfer rates due to gas and $LN_2$ vapours. Heat-sealing is commonly performed, both with existing foil materials and heat-sealing a polymer straw. In an example heat sealing arrangement, suction cups for lid pickup were positioned inside a heated sealing head. In a preferred form, the Instrument is adapted to transfer a lid from the position it is loaded in, onto the pod and this may be performed by individual suction cups and a vacuum source. The sealing of the Lid may be provided by applying pressure of about 5-8N at a temperature of nominally about 140-175° C. for approximately 2-3 seconds. Testing has shown it can be beneficial for the purposes of maintaining a stable embryo temperature to apply and use a higher temperature for less time. Conversely, for surface treated and sterilised pods a lower temperature based on seal integrity testing may be required. The optimal temperature is in the range of about 140° C. to about 155° C. A typical expected workflow for the Consumable Sealing is as follows:

Pre-heat Heat Sealer head
Move robots to position to pick up Lid
Turn on suction to secure Lid to Z-robot
Move Lid to pod position
Release Lid
Move robots to position to seal Lid for required time. In one embodiment, after this step, it is envisaged that the airflow may be reversed to blow air onto the lid.
Promptly move robots out of the way
Promptly move Cassette to unload position
Sound alarm for user unloading The embryo viability is sensitive to temperature, especially in VS4 solution. It is considered, the temperature of the embryo should not rise above 37.5° C. In certain embodiments the temperature of the embryos, preferably should not rise by more than about 5° C. during the 10 s period after sealing. These two limitations should be carefully considered as they may strongly affect design of the instrument and workflow.

Alignment of the heat seal head to the pods has been seen in preferred embodiments to affect the seal consistency. This has been catered for in design so that a consistent and even seal is created, even in the event of slight misalignment in the loading of the pods or Cassette.

The instrument should detect when a lid is not present at the instant before heat sealing and not contact that pod. This will ensure that the heat sealer does not get contaminated with melted polypropylene from the pod.

A summary of specifications and interfaces for the heat sealing is as follows:

Seal time nominally about 2.5 s±0.5 s
Temperature of seal nominally about 140° C. to about 155° C. as shown by heat seal integrity testing
Maintain accuracy of target temperature at the sealing face within ±2.5° C.
Seal force nominally about 0.08 MPa-0.2 MPa
Detect lids that are missing and prevent the heat sealer contacting bare pods
Cater for misalignment present in the pods/Lids without compromising seal Preferably a Peltier module or any other equivalent thermoelectric heat transfer device is employed in embodiments to maintain the embryos at the target protocol temperature during the equilibration steps on the Instrument. Additionally, the Peltier may preferably serve to operatively associate the pod by way of one or a combination of locating, providing thermal contact and reliably connecting, wherein locating and releasing the cassette from the Peltier may be assisted by arrangement of magnets. These functions may be able to be applied to other consumables. In this respect, the pods and media are maintained at a particular temperature throughout the protocol. As the ambient temperature in the labs may be above the minimum protocol temperature, cooling must be allowed for as well. The other motivation for cooling is to allow a shorter time between protocols of different temperatures, rather than relying on ambient thermal diffusion. To do this, the Transverse Carriage comprises an aluminium stage mounted to the X-Axis Robot, using a Peltier and a temperature sensor to maintain accurate temperature. The pods and Media Vials have good thermal conduct with the Peltier Module's interface plate, or as good a thermal contact as can be practically achieved. Accordingly, the following is considered and provided:

The instrument is adapted to run protocols with a temperature range between about 19° C. and about 37° C.
The instrument is further adapted to operate in environments between about 18° C. and about 27° C.
The instrument operating tray operates within about 0-2° C. of the intended protocol temperature achieved via appropriate software controlled temperature setting means as will appreciated by a person skilled in the art.
The temperature of fluid in the consumable and the vitrification solutions are within about 0-2° C. of each other achieved via appropriate software controlled temperature setting means as will appreciated by a person skilled in the art.
The pods and Media Vials have good thermal contact with the Peltier Module's interface plate, or as good a thermal contact as can be practically achieved.

A transverse axis robot means is provided to move the Peltier Module to each X position as required in the protocol. This may be driven by the layout decision. The Instrument may therefore have one transverse axis that moves a carriage to each x-location as required, for example, to move the heat sealers in line with the lids, or place the end of the tip into the pod to dispense. In a preferred embodiment the transverse axis means provides positional accuracy within about 0.1 mm to cater for the tolerance stack between the built Instrument, a loaded tip with its 1.016 mm runout, and any tolerance due to the fit between pods and the Carriage. This is estimated based on the above runout of tips and a reasonable tolerance stack-up due to build (in) accuracies. The means is capable of moving at estimated velocities up to approximately 100 mm/s. Either step loss should reliably not occur or step loss detection should be implemented such that the loss of steps does not cause a possible failure of any Instrument functions. The Transverse Axis and Carriage may have many interfaces, some of which are discussed in more detail below. A critical interface is between the Transverse Axis and the Z-Axis (or Gantry as it may be referred to). The core technology depends on positional accuracies that are driven by both the Transverse and Z axis. Accordingly, the Transverse Axis is mounted securely in the chassis of the instrument. The tolerance on this can be greater than to the Z-axis provided that the consumable detection system can handle it. For servicing, components of the Transverse Axis are preferably designed to be replaceable either directly in the Instrument, or by swapping out a sub-assembly.

A Z-axis robot means or gantry is provided in preferred embodiments to move the Solution Exchange and the Consumable Sealing systems in the Z-direction, to each height as required by the protocol. It is also utilised to push on the Pipette Tips to the Pipettes, and also remove the Tips from the Pipettes. Generally, the Z-axis utilises a stepper motor to drive a lead-screw/ball-screw mounted carriage. Additional support and constraint is provided to the carriage via two linear bearings mounted on the Solution Exchange side of the Gantry plate. This is because tolerances are more critical for the Tip to pod interaction compared to the heat sealing. In a preferred embodiment, tips were removed from Dispense Pumps using a tip removing feature attached to the Heated Carriage. By moving the Dispense Pumps down and then the Transverse Carriage across, the tips can be held in place by a Tip Remover whilst driving a Dispense Axis robot up to pull the disposable tips off the Dispense Pump adaptors. The space around the Transverse Carriage and the user interaction may be simplified by adding a separate simple axis to move a 'tip stripper' into place allowing tips to be stripped back into their original holder rather than requiring a separate bin.

To enable vitrification of the embryos, liquid nitrogen ($LN_2$) is required.

An example $LN_2$ storage vessel for the Instrument is represented in FIG. 9 and it is noted that a handle may be added. Accommodation for $LN_2$ is within the Instrument footprint so that for manual vitrification, the $LN_2$ bath is conveniently located for quick immersion of the Cassette when the protocol finishes. In a particular embodiment, the transfer of the Cassette to $LN_2$ for vitrification is automated. In the case of manual vitrification, the $LN_2$ capabilities detect the presence and level of the $LN_2$. In the case of automated vitrification, the Instrument preferably also transfers the Cassette from the Transverse Carriage to the $LN_2$ bath. This transfer may include agitation as determined by testing. The Instrument is adapted to detect that there is enough $LN_2$ in the bath for the Cassette to be transferred into for embryo vitrification at the end of the automated equilibration steps. For manual vitrification, it will be up to the user to ultimately ensure that they have enough $LN_2$ in a container to vitrify but the instrument should be capable of providing feedback of empty/too low, enough, etc. For automated vitrification on board, the $LN_2$ level detection/check may be part of the critical performance as if there is not enough $LN_2$ when the instrument transfers the Cassette, the embryos will not survive. In either case, the Instrument is preferably adapted to perform the check at the beginning of the protocol, preferably when it checks the presence of consumables. The $LN_2$ bath is formed to be large enough and have controlled evaporation so that within the operating environment range of the Instrument (18° C. to 27° C.), the $LN_2$ will not evaporate below the minimum required level within about 30 minutes. Preferably, the $LN_2$ should be isolated from the loading area such that an Operator does not pass their hand through $LN_2$ vapours and so that it is not easily possible to cause $LN_2$ vapours to either pass over any loaded consumables or to disturb the temperature control of the Transverse Carriage. Any removable container with $LN_2$ will preferably have a handle for OH&S reasons. On similar safety grounds, the material chosen is preferably capable of withstanding the repeated thermal shock of being at ambient temperature and having $LN_2$ poured into it. A preferred product is manufactured from HDPE.

To reduce the size of a bath that can last 30 minutes, several factors may reduce the $LN_2$ evaporation rate. In this respect, the insulation properties of the bath itself may most likely have the greatest effect. Also, the addition of a lid will further reduce the evaporation rate of the $LN_2$. In summary, the instrumentation's accommodation for LN2 may be summarised as follows:

Should store enough $LN_2$ to last about 30 minutes in ambient between about 18° C. and about 27° C.

Fits into the Instrument chassis and covers

Geometry ensures that after about 30 minutes, all pods in a Cassette remain submerged Include a lid for use off the instrument Include a handle for OH&S reasons when transporting the container with $LN_2$ in it.

All subsystem assemblies of the instrumentation mount to a chassis. The subsystems are preferably located precisely as any misalignments may add to create misalignment at the pod. This could have severe consequences such as incorrect positioning of the tip in the pod or failure to align the lids on the pods.

A preferred embodiment has incorporated a sub-module that isolates all of the systems involved in operations of high accuracy. These critical operations involve interactions between items on the Transverse Carriage and either of the Solution Exchange or Consumable Sealing systems. To minimise the compounding requirements for tolerances, a combined 'gantry' and transverse module are provided that can be assembled into the main chassis. The main chassis can then have 'standard' tolerances for general fit of components. In a preferred embodiment the instrument dimensions and weight correspond to maximum dimensions of about 750 mm wide×about 700 mm deep ×about 600 mm high with a maximum weight of about 45 kg.

As a suitable user interface, a colour touchscreen display is used for user control of the Instrument, for example, an LCD touchscreen. FIG. 10 shows example screenshots of a GUI in a preferred embodiment. Whilst other display options may provide the functionality, it is considered that current market expectations demand a colour touchscreen to control an instrument of this level of technology and a GUI embodies such a user interface. In a preferred embodiment the GUI comprises 5.7" display whereas other embodiments involve different screen sizes such as a 4.3" display. Resistive and capacitive touchscreens are considered suitable. A resistive touchscreen is provided in a preferred embodiment on the basis of its competitive and development time. Ordinarily, no alcohol or aromatics are allowed in clinical laboratories and only mild soap and water are typically allowed for cleaning so there is no specific requirement for a glass cover over the screen but this may be provided.

Logging of data may occur in two forms. One level of logging is such that it will only be accessed by service personnel and will log detailed instrument data for each protocol run. The other level of logging will log data relevant for confirming details of the protocol used for an embryo warmed at a later date, included high-level instrument function confirmation (eg temperature of Carriage). These "logs" may be tracked by a unique identifier, and time and date stamp.

Overall, the instrument in preferred embodiments is designed in accordance with an appropriate standard such as for example, 'ANSI/AAMI/IEC 62366:2007 Medical devices—Application of usability engineering to medical devices' using guidance from the standard, 'ANSI/AAMI HE75:2009 Human factors engineering—Design of medical devices'.

With respect to safety considerations, in preferred embodiments the instrument will follow the international standard, IEC 61010 or the equivalent as dictated by regulatory requirements. A hazard analysis may be conducted to identify areas requiring attention to increase safety.

All subassemblies that have components which may wear or fail have been designed with an appropriate level of replacement in mind. For example, Peltiers may fail or bearings or guides may wear, leading to potential failure. Where practical, these have been designed to be relatively easily replaced.

Consumables and Accessories

The pod in preferred embodiments allows for automated fluid exchange and vitrification of an embryo. Embryos are typically approximately about 50 μm-300 μm in diameter although during the process, they may collapse and re-expand so at times they are much smaller than this. The vitrification process requires that the embryo be exposed to several solutions for specific durations and at specific temperatures to replace water in and around the embryo cell(s) with cryoprotectants to eliminate or reduce the damage due to cryopreservation and, as noted above, typically damage is due to ice crystals. In accordance with preferred embodiments, the pod device prevents the embryo being drawn up with aspirated fluid but allows fluid exchange to take place and allow for high heat transfer rates in a 'closed' system. A 'closed' system in this case refers to a vitrification system that prevents direct contact between $LN_2$ and the embryo. FIGS. 15 to 18 illustrate a typical pod in accordance with preferred embodiments of the present invention. Essentially the pod of preferred embodiments comprises three components, namely, a carrier for support, a lid and a channel. The channel includes a divot for accommodating the specimen embryo, which is described in published PCT specification No. WO 2011/146998. The preferred pod design has the following features:

- Allow easy loading by clearly identifiable embryo placement region by virtue of the divot, as shown in FIG. 18
- May be optically transparent for the purpose of assisting the operator to locate the embryo
- May have wettable surface to allow fluid to be exchanged over the embryo
- Hermetically sealed to prevent $LN_2$ contamination
- Allow a vitrification and warming rate faster than about 7,000° C./min
- Minimise carryover of solutions (eg between Buffer Solution and Equilibration Solution, and between Equilibration Solution and Vitrification Solution)
- Work for different types and developmental ages and stages of embryos. For example, must work for human embryos but must also work for mouse embryos due to development requirements, and must have at least potential (pending further protocol optimisation) work for embryos other mammalian and non-mammalian species. It may work for oocytes through to fully hatched blastocysts
- Meet the recovery and survival rate as per currently established closed manual process(es)
- Allow for one embryo and up to two oocytes to be vitrified in the same vessel when used with human embryos
- Allow for warming and re-equilibration of the embryo and oocyte
- The pod should be easily opened by a user
- The pod should allow for the embryo to be easily found after warming. This also dictates that the pod has good optical clarity and not have geometry that obstructs viewing of the embryo.
- The pod can be sterilized at between about 20 kGy and about 35 kGy (nominally 25 kGy)
- The pod will allow heat sealing to aluminium/polyprop laminate material. This requires that the sealing face on the pod be polypropylene/polyethylene
- Peelable heat seal in comparison to destructive heat seal The above functions are performed despite the added complexity that embryos are living cells, very small (at about 50-300µm), fragile, not readily available, change shape during the process, floats, and are very sensitive etc.

In a preferred embodiment four pods are stored in a cassette, which serves also as the final storage container to be placed in $LN_2$ tanks, without reducing current storage capacity in the $LN_2$ or $LN_2$ liquid or vapour storage tanks. The pods are also adapted to fit onto the Transverse Carriage well so that there is adequate heat transfer to maintain good temperature control during processing.

The pod channel is preferably manufactured separately and it could be combined into a single unitary part. The pods are adapted to fit onto the Transverse Carriage well so that there is adequate heat transfer to maintain good temperature control during processing. The channel is wettable by way of surface treatment or other modifications. Many surface treatments were tested including but not limited to flame treatment, chemical, corona and plasma treatment. The pod is preferably treated by plasma treatment. Optical clarity of the Channel is relevant to its usability. The Channel is adapted to seal to the Carrier to be impermeable to $LN_2$. The maximum volume of fluid that can be added to a pod is about 55 µL. The Carrier is the part of the pod that will carry the label and provide the means to handle the Channel. In this respect it provides space for $LN_2$, proof labelling and an appropriate surface. The carrier attaches to the Cassette at room temperature down to about −196° C. and may be removable in the same temperature range.

In general the Lid will contain Aluminium/polypropylene laminated heat seal as abovementioned, and will be sealed to the pod Channel and Carrier. The Lid is designed such that it is easily removed upon warming for prompt addition of the re-equilibration solutions.

A Cassette is the part that will hold any suitable number, preferably up to four, pods at a time and an example is shown in FIG. 12. It is a replacement for the 'canes' used in current systems to store multiple vitrification devices such as hooks, Cryotop®, straws etc from the same patient in the $LN_2$ or vapour storage tanks. The cassette preferably includes a handle that allows a user to hold the Cassette to vitrify the embryos in the pods. The Cassette is also equipped to have adequate area for a barcode and other ID. In one form the cassette is adapted for some form of ID to be readable from above a Canister full of Cassettes, as shown in FIG. 12. The cassette preferably has the following features:

- It is easy and intuitive to load and unload a pod, by virtue of the characteristic shape design of the carrier of the pod.
- It is easy to quickly dunk and agitate the Cassette in $LN_2$ without a user burning their fingers.
- When attempting to retrieve a particular Cassette from storage, a user will want to be able to identify that Cassette without removing other Cassettes from a Canister or other storage form.
- Needs to fit to pitch of about 28.5 mm With reference to interfaces with the pods, the pods are adapted for easy insertion into the Cassette at room temperature. When loaded onto the instrument, the pods are able to move to locate to the Carriage rather than being restricted by the Cassette. Pods are removable under $LN_2$ or vapours and do not readily fall out of Cassette. To enable a consistent removal of the pod from the cassette, repeatable force is applied by magnets appropriately positioned which are adapted to exercise magnetic field strength of given magnitude upon the ferrous metal residing in the pod. To this end the magnets are preferably positioned in distributed locations within the cassettes. The cassette interfaces with the Instrument via the Carriage and interfaces with a Canister in storage. Further, the cassette is easily removable from the Canister whilst keeping all embryos within either $LN_2$ or vapour. The pod may be designed with enough buoyancy to float in the case it was to be separated from the cassette in the $LN_2$ tank.

With reference to FIG. 14, a consumable tray is provided for vials of vitrification solutions, waste, and pipette tips. It sits flat on a bench or hot plate and allows heat transfer through to the pod and solutions. It is also easily handled and easily and accurately loaded into position on the Heated Carriage. The pods are located in the Consumable Tray by the fit of the Cassette and also channel features on the Consumable Tray that aid heat transfer to the solutions within the pod. The vials are close-fitting into the Consumable Tray for both location and heat transfer reasons.

The Consumable Tray is also adapted to allow the consumables to pass under the various stations at a low clearance height to reduce the Z-axis travels for each station. The tips however are preferably much higher than the other components. Given this requirement and the requirement to rest flat on a bench, the Tray has been designed with a floating tip holder so that it can rest high when on a bench or hot plate, and rest low within a cut-out when loaded on the instrument. Tips may be loaded by driving the Dispense Axis down into the tips against their holder in the Consumable Tray. The force to pick up tips is about 60-100N (6-10 kg) vertically down. The tray is adapted to fit to pitch of about 28.5 mm and is adapted to positively engage into the instrument with and overall maximum height of about 60 mm.

A media cartridge may be provided with features including the following. It is adapted to hold at least two fluid vials in a removable and sterile fashion. The media cartridge is adapted to fit to pitch of about 28.5 mm. It can maximise heat exchange to the media vials and is adapted for positive engagement of the media vials. Media vials may be provided which contain a minimum of about 100 μL solution and are determined by what is suitable for media production and shelf-life.

A tip cartridge is provided with the following features. The force required to pick up tips is about 60-100N (6-10 kg) vertically down. The tip cartridge holds at least one clear waste vial for post protocol embryo checking and holds at least one sterile pipette tips. It holds at least one sterile heat sealable Lid and fits to a pitch of about 28.5 mm. It minimises storage volume for dry components. It also provides for tip removal back into the consumable/disposable for disposal.

A dispense tip is provided and an OEM tip is preferable. In one embodiment the 10 μL filtered Axygen™ TF300 tip has been used. Features and design considerations for the dispense tip include that the tip has a fine distal end such that it can fit inside the pod channel, allowing for tolerances of the pod, tip and instrument. The tip is adapted to hold a minimum of about 10 μL and it should be filtered. It is also preferable that the dispense tip is adapted for interaction with pipette tips.

With reference to FIG. 14 canisters are provided for use as containers to hold a number of Cassettes in storage tanks or dewars. Current systems use canisters to hold Canes, which then hold a number of straws, or other vitrification devices. In this embodiment the exemplary canisters are designed for the following systems: $LN_2$ storage tanks; $LN_2$ vapour phase storage tanks, dry shippers and Dewar storage systems.

With respect to Dewar Storage, there is capacity for 16 small canes @3-6 embryos each, or alternatively 4 large canes @7 embryos each. Canister capacity is equivalent to about 20 patients ie, 76 embryos which equates to total capacity. With respect to tank storage, there is capacity for 16 small canes @3 embryos each, or alternatively 10 large canes @7 embryos each. Canister capacity is equivalent to about 26 patients ie, 118 embryos. With a 2-Canister stack there is capacity equivalent to about 52 patients ie, 236 embryos.

A potential need has been identified for a pod removal tool to aid removing pod from a Cassette whilst still in $LN_2$ or vapours. This would only be required if the removal of pods is difficult in the pod and Cassette designs. However, in contrast it is preferable to use the magnet position system as described above.

For reference, it has been observed that due to the increase rigidity of the plastics at cryogenic temperatures, features that are normally designed to flex for engagement and release are no longer able to under a user-friendly force.

While this invention has been described in connection with specific embodiments thereof, it will be understood that it is capable of further modification(s). This application is intended to cover any variations uses or adaptations of the invention following in general, the principles of the invention and including such departures from the present disclosure as come within known or customary practice within the art to which the invention pertains and as may be applied to the essential features hereinbefore set forth.

As the present invention may be embodied in several forms without departing from the spirit of the essential characteristics of the invention, it should be understood that the above described embodiments are not to limit the present invention unless otherwise specified, but rather should be construed broadly within the spirit and scope of the invention as defined in the appended claims. The described embodiments are to be considered in all respects as illustrative only and not restrictive.

Various modifications and equivalent arrangements are intended to be included within the spirit and scope of the invention and appended claims. Therefore, the specific embodiments are to be understood to be illustrative of the many ways in which the principles of the present invention may be practiced. In the following claims, means-plus-function clauses are intended to cover structures as performing the defined function and not only structural equivalents, but also equivalent structures. For example, although a nail and a screw may not be structural equivalents in that a nail employs a cylindrical surface to secure wooden parts together, whereas a screw employs a helical surface to secure wooden parts together, in the environment of fastening wooden parts, a nail and a screw are equivalent structures.

It should be noted that where the terms "server", "secure server" or similar terms are used herein, a communication device is described that may be used in a communication system, unless the context otherwise requires, and should not be construed to limit the present invention to any particular communication device type. Thus, a communication device may include, without limitation, a bridge, router, bridge-router (router), switch, node, or other communication device, which may or may not be secure.

It should also be noted that where a flowchart is used herein to demonstrate various aspects of the invention, it should not be construed to limit the present invention to any particular logic flow or logic implementation. The described logic may be partitioned into different logic blocks (e.g., programs, modules, functions, or subroutines) without changing the overall results or otherwise departing from the true scope of the invention. Often, logic elements may be added, modified, omitted, performed in a different order, or implemented using different logic constructs (e.g., logic gates, looping primitives, conditional logic, and other logic constructs) without changing the overall results or otherwise departing from the true scope of the invention.

Various embodiments of the invention may be embodied in many different forms, including computer program logic for use with a processor (e.g., a microprocessor, microcontroller, digital signal processor, or general purpose computer and for that matter, any commercial processor may be used to implement the embodiments of the invention either as a single processor, serial or parallel set of processors in the system and, as such, examples of commercial processors include, but are not limited to Merced™, Pentium™, Pentium II™, Xeon™, Celeron™, Pentium Pro™, Efficeon™, Athlon™, AMD™ and the like), programmable logic for use with a programmable logic device (e.g., a Field Programmable Gate Array (FPGA) or other PLD), discrete components, integrated circuitry (e.g., an Application Specific Integrated Circuit (ASIC)), or any other means including any combination thereof. In an exemplary embodiment of the present invention, predominantly all of the communication between users and the server is implemented as a set of computer program instructions that is converted into a computer executable form, stored as such in a computer readable medium, and executed by a microprocessor under the control of an operating system.

Computer program logic implementing all or part of the functionality where described herein may be embodied in various forms, including a source code form, a computer executable form, and various intermediate forms (e.g., forms generated by an assembler, compiler, linker, or locator). Source code may include a series of computer program instructions implemented in any of various programming languages (e.g., an object code, an assembly language, or a high-level language such as Fortran, C, C++, JAVA, or HTML. Moreover, there are hundreds of available computer languages that may be used to implement embodiments of the invention, among the more common being Ada; Algol; APL; awk; Basic; C; C++; Conol; Delphi; Eiffel; Euphoria; Forth; Fortran; HTML; Icon; Java; Javascript; Lisp; Logo; Mathematica; MatLab; Miranda; Modula-2; Oberon; Pascal; Perl; PL/I; Prolog; Python; Rexx; SAS; Scheme; sed; Simula; Smalltalk; Snobol; SQL; Visual Basic; Visual C++; Linux and XML.) for use with various operating systems or operating environments. The source code may define and use various data structures and communication messages. The source code may be in a computer executable form (e.g., via an interpreter), or the source code may be converted (e.g., via a translator, assembler, or compiler) into a computer executable form.

The computer program may be fixed in any form (e.g., source code form, computer executable form, or an intermediate form) either permanently or transitorily in a tangible storage medium, such as a semiconductor memory device (e.g, a RAM, ROM, PROM, EEPROM, or Flash-Programmable RAM), a magnetic memory device (e.g., a diskette or fixed disk), an optical memory device (e.g., a CD-ROM or DVD-ROM), a PC card (e.g., PCMCIA card), or other memory device. The computer program may be fixed in any form in a signal that is transmittable to a computer using any of various communication technologies, including, but in no way limited to, analog technologies, digital technologies, optical technologies, wireless technologies (e.g., Bluetooth), networking technologies, and inter-networking technologies. The computer program may be distributed in any form as a removable storage medium with accompanying printed or electronic documentation (e.g., shrink wrapped software), preloaded with a computer system (e.g., on system ROM or fixed disk), or distributed from a server or electronic bulletin board over the communication system (e.g., the Internet or World Wide Web).

Hardware logic (including programmable logic for use with a programmable logic device) implementing all or part of the functionality where described herein may be designed using traditional manual methods, or may be designed, captured, simulated, or documented electronically using various tools, such as Computer Aided Design (CAD), a hardware description language (e.g., VHDL or AHDL), or a PLD programming language (e.g., PALASM, ABEL, or CUPL). Hardware logic may also be incorporated into display screens for implementing embodiments of the invention and which may be segmented display screens, analogue display screens, digital display screens, CRTs, LED screens, Plasma screens, liquid crystal diode screen, and the like.

Programmable logic may be fixed either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM or DVD-ROM), or other memory device. The programmable logic may be fixed in a signal that is transmittable to a computer using any of various communication technologies, including, but in no way limited to, analog technologies, digital technologies, optical technologies, wireless technologies (e.g., Bluetooth), networking technologies, and internetworking technologies. The programmable logic may be distributed as a removable storage medium with accompanying printed or electronic documentation (e.g., shrink wrapped software), preloaded with a computer system (e.g., on system ROM or fixed disk), or distributed from a server or electronic bulletin board over the communication system (e.g., the Internet or World Wide Web).

"Comprises/comprising" and "includes/including" when used in this specification is taken to specify the presence of stated features, integers, steps or components but does not preclude the presence or addition of one or more other features, integers, steps, components or groups thereof. Thus, unless the context clearly requires otherwise, throughout the description and the claims, the words 'comprise', 'comprising', 'includes', 'including' and the like are to be construed in an inclusive sense as opposed to an exclusive or exhaustive sense; that is to say, in the sense of "including, but not limited to".

The invention claimed is:

1. Apparatus for micromanipulation of biological material comprising an embryo, said apparatus comprising a vessel having a reservoir with a channel formed in a portion of said reservoir, said channel comprising walls of a thickness in the range of about 0.01 mm to about 0.90 mm and an intermediate restriction dimensioned to resist passage of said biological material but allow passage of liquid treatment solutions comprising cryoprotectants,
    wherein the apparatus comprises a two-part construction such that two portions of the apparatus are adapted to be heat-sealed with a secondary material intermediate the two portions, the secondary material is a laminate adapted to prevent ingress of $LN_2$ to the apparatus and wherein the secondary material allows for peeling separation of the two part construction.

2. Apparatus as claimed in claim 1 wherein the channel further comprises a divot having a volume of between about 0.04 µl to about 0.30 µl adapted for retaining and/or positioning an embryo therein within at least a modicum of solution and wherein the surface of the channel exposed to biological material and liquid treatment solutions is surface treated to allow fluid to wet and spread out upon the surface of the channel.

3. Apparatus as claimed in claim 1 wherein the wall thickness is in the range about 0.08 mm-to about 0.12 mm.

4. A system for automated vitrification of a biological specimen comprising an embryo, the system comprising one or combination of:
    an operating tray accommodating at least one or more cartridges and/or cassettes containing solutions, consumables and at least one biological specimen comprising an embryo for use in a vitrification protocol;

a single X-axis robot for transverse movement of the operating tray to respective locations for vitrification protocol functions comprising one or a combination of solution exchange, heat sealing and lid transfer;

a gantry operatively associated with the single X-axis robot for vertical movement of protocol modules to engage the operating tray at selected locations of the transverse movement to provide one or a combination of solution exchange and heat sealing;

a software operable means for controlling the temperature environment;

a software operable means for controlling fluid dispense volume and velocity and aspiration volume and velocity for the application of liquid treatment solutions comprising cryoprotectants to the biological specimen, and;

a software operable means for controlling protocol time;

wherein the system is adapted to a carrier for handling and support of the apparatus as claimed in claim 1 within a cassette.

5. The system of claim 4 wherein the temperature is controlled in a range of about 19° C. to about 37° C.

6. The system of claim 4 wherein the fluid dispense and aspiration volume is controlled to a range of about 0.1 μl to about 15 μl with an accuracy of 1 μl±0.2 μl to 10 μl±1 μl.

7. The system of claim 4 wherein the fluid dispense and aspiration velocity is controlled in a range from about 0.01 μl/s to about 5 μl/s.

8. A system for micromanipulation of biological material comprising an embryo, the system comprising:

an operating tray accommodating at least one or more cartridges and/or cassettes containing solutions, consumables and at least one biological specimen comprising an embryo for use in a vitrification protocol;

one or a combination of independent single axis robot arms where each single axis robot arm is mounted to a static assembly wherein a combination of robot arms provides a global coordinate system for movement in at least two degrees of freedom to provide transverse movement of the operating tray to respective locations for vitrification protocol functions comprising one or a combination of solution exchange, heat sealing and lid transfer;

said system being adapted to a carrier for handling and support of an apparatus as claimed in claim 1 through at least two or a combination of the following process steps:

embryo loading;
equilibration;
heat sealing;
vitrification.

9. A method for in vitro fertilization procedures utilising apparatus as claimed in claim 1, the method comprising the steps of:

loading at least one embryo into the apparatus in a buffer solution;

replacing the buffer solution with an equilibration solution at a predetermined flow rate;

equilibrating the loaded embryo in the equilibrating solution for a predetermined equilibration time period;

replacing the equilibrating solution with a vitrification solution at a predetermined flow rate;

heat sealing the apparatus;

plunging the apparatus into a liquid cooling bath.

10. Apparatus as claimed in claim 1 wherein the apparatus is adapted for an automated vitrification process by including a carrier for handling and support of the apparatus in a cassette configured for one or a combination of:

loading into a tray for carriage on a single axis robot arm of an automated vitrification instrument, and;

interfacing with locations within the automated vitrification instrument for individual vitrification process functions.

11. Apparatus adapted to micromanipulate biological material, said apparatus including:

processor means adapted to operate in accordance with a predetermined instruction set, said apparatus, in conjunction with said instruction set together with the system of claim 4 and the apparatus of claim 10, being adapted to control the timing, temperature dispensing volumes and flow velocity involved in performing the method steps as claimed in claim 9.

12. Apparatus as claimed in claim 11 wherein the predetermined instruction set comprises computer software adapted for a controlling fluid exchange performed by a fluidics mechanism in the system of claim 4 to allow for a gradual increase in the concentration of the vitrification solution so as to decrease an osmotic shock to the embryo and increase cryopreservation quality.

13. Apparatus as claimed in claim 1 wherein the two portions comprise polymer material.

14. Apparatus as claimed in claim 13 wherein the polymer material comprises polypropylene.

* * * * *